US007611706B2

(12) United States Patent
Harkins et al.

(10) Patent No.: US 7,611,706 B2
(45) Date of Patent: Nov. 3, 2009

(54) RG1 ANTIBODIES AND USES THEREOF

(75) Inventors: Richard Harkins, Alameda, CA (US);
Deborah Parkes, Hayward, CA (US);
Gordon Parry, Oakland, CA (US);
Renate Parry, Oakland, CA (US);
Douglas Schneider, Lafayette, CA (US)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 11/981,219

(22) Filed: Oct. 30, 2007

(65) Prior Publication Data

US 2008/0226656 A1 Sep. 18, 2008

Related U.S. Application Data

(62) Division of application No. 10/895,183, filed on Jul. 20, 2004, now Pat. No. 7,335,748.

(60) Provisional application No. 60/489,032, filed on Jul. 22, 2003.

(51) Int. Cl.
*A61K 39/395* (2006.01)
*C12P 21/04* (2006.01)
*C12P 21/08* (2006.01)
*C07H 21/04* (2006.01)
*C07K 16/00* (2006.01)

(52) U.S. Cl. ............. 424/142.1; 424/130.1; 424/141.1; 424/155.1; 424/181.1; 435/69.6; 435/70.21; 530/387.1; 530/388.1; 530/388.15; 530/388.8; 530/391.3; 530/391.7

(58) Field of Classification Search ........................ None
See application file for complete search history.

(56) References Cited

U.S. PATENT DOCUMENTS

| 4,831,175 | A | 5/1989 | Gansow et al. |
|---|---|---|---|
| 5,246,692 | A | 9/1993 | Gansow et al. |
| 5,804,382 | A | 9/1998 | Sytkowski et al. |
| 5,871,969 | A | 2/1999 | Hastings et al. |
| 5,877,397 | A | 3/1999 | Lonberg et al. |
| 6,150,584 | A | 11/2000 | Kucherlapati et al. |
| 6,300,129 | B1 | 10/2001 | Lonberg et al. |
| 6,682,736 | B1 | 1/2004 | Hanson et al. |
| 6,682,902 | B2 | 1/2004 | Harkins et al. |
| 6,824,780 | B1 | 11/2004 | Devaux et al. |
| 2003/0059427 | A1 | 3/2003 | Force et al. |
| 2004/0120948 | A1 | 6/2004 | Mikayama et al. |

FOREIGN PATENT DOCUMENTS

| EP | 1 262 193 A1 | 12/2002 |
|---|---|---|
| WO | WO98/45442 | 10/1998 |
| WO | WO98/50073 | 11/1998 |
| WO | WO99/46281 | 9/1999 |
| WO | WO00/23108 | 4/2000 |
| WO | WO01/44291 | 6/2001 |
| WO | WO02/088186 | 11/2002 |
| WO | WO03/031475 | 4/2003 |

OTHER PUBLICATIONS

Umemiya et al., "M-Spondin, a novel ECM protein highly homologous to vertebrate F-spondin, is localized at the muscle attachment sites in the Drosophila embryo," *Develop. Biol.*, 1997, 186:165-76 (Exhibit 9).
Manda et al., "Identification of genes (SPON2 and C2Oorf2) differentially expressed between cancerous and noncancerous lung cells by mRNA differential display," *Genomics*, 1999, 61:5-14 (Exhibit 10).
Klar et al., "F-spondin: a gene expressed at high levels in the floor plate encodes a secreted protein that promotes neural cell adhesion and neurite extension," *Cell*, 1992, 69:95-110 (Exhibit 11).
Feinstein et al., "F-spondin and mindin: two structurally and functionally related genes expressed in the hippocampus that promote outgrowth of embryonic hippocampal neurons," *Development*, 1999, 126:3637-48 (Exhibit 12).
Burstyn-Cohen et al., "Accumulation of F-spondin in injured peripheral nerve promotes the outgrowth of sensory axons," *J. Neuroscience*, 1998, 18:8875-85 (Exhibit 13).
Higashijima et al., Mindin/F-Spondin Family: Novel ECM Proteins Expressed in the Zebrafish Embryoic Axis, *Developmental Biology*, 1997, 192:211-27 (Exhibit 14).
Sodee et al., "Preliminary Imaging Results Using In-11 Labeled CYT-356 (Prostascint™) in the Detection of Recurrent Prostate Cancer," *Clinical Nuclear Medicine*, 1996, 21:759-67 (Exhibit 15).
Mikayama et al., "Molecular cloning and functional expression of cDNA encoding glycosylation-inhibiting factor," *PNAS*, 1993, 90:10056-60 (Exhibit 16).
Ngo et al., "Computational Complexity, Protein Structure Prediction, and the Levinthal Paradox," in *The Protein Folding Problem and Tertiary Structure Prediction*, 1994, ed. Birkhauser, Boston, MA, pp. 433 and 492-5 (Exhibit 17).
Saini et al., "Regulation of the turnover of mRNAs encoding cellular oncoproteins," *Biochem. Cell Biol.*, 1991, 69:415-7 (Exhibit 18).
Hershey, "Protein Phosphorylation Controls Transition Rates," *J. Biol. Chem.*, 1989, 264:20832-6 (Exhibit 19).
Fan, Z-H et al., "Enhancement of Nitric Oxide Production from Activated Macrophages by Purified Form of Ginsenoside (RG1)," *The Great American Journal of Chinese Medicine*, 1995, 23:279-87 (Exhibit 26).
Borrebaeck, Carl A. K. et al., "Kinetic Analysis of Recombinant Antibody—Antigen Interactions: Relation Between Structural Domains and Antigen Binding," *Bio/Technology*, 1992, 10:697-8 (Exhibit 27).
Little, M. et al., "Of mice and men: hybridoma and recombinant antibodies," *Immunology Today*, 2000, 21:364-70 (Exhibit 28).

(Continued)

*Primary Examiner*—David J. Blanchard
(74) *Attorney, Agent, or Firm*—Mandel & Adriano

(57) ABSTRACT

The present invention relates to antibodies, and antigen-binding antibody fragments, directed against an RG1 polypeptide. The invention further relates to methods for utilizing the antibodies, and antibody fragments, for diagnostic and therapeutic applications.

12 Claims, 4 Drawing Sheets

OTHER PUBLICATIONS

*Fundamental Immunology*, William E. Paul, ed., New York, NY, 1993, pp. 292-295 (Exhibit 33).

Rudikoff, Stuart et al., "Single amino acid substitution altering antigen-binding specificity," *Proc. Natl. Acad. Sci. USA*, 1982, 79:1979-83 (Exhibit 34).

Colman, P. M., "Effects of amino acid sequence changes on antibody-antigen interactions," *Research in Immunology*, 1994, 145:33-6 (Exhibit 35).

Holliger, Philipp et al., "Diabodies': Small bivalent and bispecific antibody fragments," *Proc. Natl. Acad. Sci. USA*, 1993, 90:6444-8 (Exhibit 36).

FIGURE 3 huMAb B Variable Region Sequences $V_L$

```
  1 METPAQLLFLLLLWLPDTTGEIVLTQSPGTLSLSPGERATLSCRASQSVS  50
 51 SSYLAWYQQKPGQAPRLLIYGASSRATGIPDRFSGSGSGTDFTLTISRLE 100
101 PEDFAVYYCQQYSSSLTFGGGTKVEIK                       150
```

$V_H$

```
  1 MEFVLSWVFLVAILKGVQCEVQLVQSGGGLVHPGGSLRLSCAGSGFTFSS  50
 51 YVMHWLRQAPGKGLEWVSVIGTGGVTHYADSVKGRFTISRDNAKNSLYLQ 100
101 MNSLRAEDMAMYYCARWGYYGSGSYENDAFDIWGQGTMVTVSSASTK   150
```

B_3M, $V_H$ (mutations in bold)

```
  1 MEFVLSWVFLVAILKGVQCEVQLVQSGGGLVQPGGSLRLSCAGSGFTFSS  50
 51 YVMHWLRQAPGKGLEWVSVIGTGGVTHYADSVKGRFTISRDNAKNSLYLQ 100
101 MNSLRAEDTAVYYCARWGYYGSGSYENDAFDIWGQGTMVTVSSASTK   150
```

CDR sequences (1,2,and 3) for each variable region are underlined

FIGURE 4

HuMAb C Variable Region Sequences $V_L$

```
  1 METPAQLLFLLLLWLPDTTGEIVLTQSPGTLSLSPGERATLSCRASQSVS  50
 51 SSYLAWYQQKPGQAPRLLIYGASSRATGIPDRFSGSGSGTDFTLTISRLE 100
101 PEDFAVYYCQQYGSSLTFGGGTKVEIK                        150
```

$V_H$

```
  1 MEFVLSWVFLVAILKGVQCEVQLVQSGGGLVHPGGSLRLSCAGSGFTFSS  50
 51 YVMHWVRQAPGKGLEWVSVIGTGGVTNYADSVKGRFTISRDNAKNSLYLQ 100
101 MNSLRAEDMAVYYCARWGDWDDAFDIWGQGTMVTVSSASTK          144
```

C_2m, $V_H$          (mutations in bold)

```
  1 MEFVLSWVFLVAILKGVQCEVQLVQSGGGLVQPGGSLRLSCAGSGFTFSS  50
 51 YVMHWVRQAPGKGLEWVSVIGTGGVTNYADSVKGRFTISRDNAKNSLYLQ 100
101 MNSLRAEDTAVYYCARWGDWDDAFDIWGQGTMVTVSSASTK          144
```

CDR sequences (CDR1,2,3) for each variable region are underlined

SEQUENCE LISTING

```
<160> NUMBER OF SEQ ID NOS: 31

<210> SEQ ID NO 1
<211> LENGTH: 1785
<212> TYPE: DNA
<213> ORGANISM: Homo sapiens
<220> FEATURE:
<221> NAME/KEY: CDS
<222> LOCATION: (296)..(1291)

<400> SEQUENCE: 1
agaaaggggt gcggcagcac tgccagggga agagggtgat ccgacccggg gaaggtcgct      60
gggcagggcg agttgggaaa gcggcagccc ccgccgcccc cgcagcccct tctcctcctt     120
```

-continued

```
tctcccacgt cctatctgcc tctcgctgga ggccaggccg tgcagcatcg aagacaggag       180
gaactggagc tcattggcc ggcccggggc gccggcctcg gcttaaata ggagctccgg        240 gctctggctg ggacccgacc gctgccggcc gcgctcccgc tgctcctgcc gggtg atg      298
                                                                Met
                                                                 1 gaa aac ccc agc ccg gcc gcc gcc ctg ggc aag gcc ctc tgc gct ctc         346
Glu Asn Pro Ser Pro Ala Ala Ala Leu Gly Lys Ala Leu Cys Ala Leu
          5                  10                  15 ctc ctg gcc act ctc ggc gcc gcc ggc cag cct ctt ggg gga gag tcc         394
Leu Leu Ala Thr Leu Gly Ala Ala Gly Gln Pro Leu Gly Gly Glu Ser
         20                  25                  30 atc tgt tcc gcc gga gcc ccg gcc aaa tac agc atc acc ttc acg ggc         442
Ile Cys Ser Ala Gly Ala Pro Ala Lys Tyr Ser Ile Thr Phe Thr Gly
     35                  40                  45 aag tgg agc cag acg gcc ttc ccc aag cag tac ccc ctg ttc cgc ccc         490
Lys Trp Ser Gln Thr Ala Phe Pro Lys Gln Tyr Pro Leu Phe Arg Pro
 50                  55                  60                  65 cct gcg cag tgg tct tcg ctg ctg ggg gcc gcg cat agc tcc gac tac         538
Pro Ala Gln Trp Ser Ser Leu Leu Gly Ala Ala His Ser Ser Asp Tyr
                 70                  75                  80 agc atg tgg agg aag aac cag tac gtc agt aac ggg ctg cgc gac ttt         586
Ser Met Trp Arg Lys Asn Gln Tyr Val Ser Asn Gly Leu Arg Asp Phe
             85                  90                  95 gcg gag cgc ggc gag gcc tgg gcg ctg atg aag gag atc gag gcg gcg         634
Ala Glu Arg Gly Glu Ala Trp Ala Leu Met Lys Glu Ile Glu Ala Ala
        100                 105                 110 ggg gag gcg ctg cag agc gtg cac gcg gtg ttt tcg gcg ccc gcc gtc         682
Gly Glu Ala Leu Gln Ser Val His Ala Val Phe Ser Ala Pro Ala Val
    115                 120                 125 ccc agc ggc acc ggg cag acg tcg gcg gag ctg gag gtg cag cgc agg         730
Pro Ser Gly Thr Gly Gln Thr Ser Ala Glu Leu Glu Val Gln Arg Arg
130                 135                 140                 145 cac tcg ctg gtc tcg ttt gtg gtg cgc atc gtg ccc agc ccc gac tgg         778
His Ser Leu Val Ser Phe Val Val Arg Ile Val Pro Ser Pro Asp Trp
                150                 155                 160 ttc gtg ggc gtg gac agc ctg gac ctg tgc gac ggg gac cgt tgg cgg         826
Phe Val Gly Val Asp Ser Leu Asp Leu Cys Asp Gly Asp Arg Trp Arg
            165                 170                 175 gaa cag gcg gcg ctg gac ctg tac ccc tac gac gcc ggg acg gac agc         874
Glu Gln Ala Ala Leu Asp Leu Tyr Pro Tyr Asp Ala Gly Thr Asp Ser
        180                 185                 190 ggc ttc acc ttc tcc tcc ccc aac ttc gcc acc atc ccg cag gac acg         922
Gly Phe Thr Phe Ser Ser Pro Asn Phe Ala Thr Ile Pro Gln Asp Thr
    195                 200                 205 gtg acc gag ata acg tcc tcc tct ccc agc cac ccg gcc aac tcc ttc         970
Val Thr Glu Ile Thr Ser Ser Ser Pro Ser His Pro Ala Asn Ser Phe
210                 215                 220                 225 tac tac cca cgg ctg aag gcc ctg cct ccc atc gcc agg gtg aca ctg        1018
Tyr Tyr Pro Arg Leu Lys Ala Leu Pro Pro Ile Ala Arg Val Thr Leu
                230                 235                 240 gtg cgg ctg cga cag agc ccc agg gcc ttc atc cct ccc gcc cca gtc        1066
Val Arg Leu Arg Gln Ser Pro Arg Ala Phe Ile Pro Pro Ala Pro Val
            245                 250                 255 ctg ccc agc agg gac aat gag att gta gac agc gcc tca gtt cca gaa        1114
Leu Pro Ser Arg Asp Asn Glu Ile Val Asp Ser Ala Ser Val Pro Glu
        260                 265                 270
```

```
acg ccg ctg gac tgc gag gtc tcc ctg tgg tcg tcc tgg gga ctg tgc    1162
Thr Pro Leu Asp Cys Glu Val Ser Leu Trp Ser Ser Trp Gly Leu Cys
    275                 280                 285 gga ggc cac tgt ggg agg ctc ggg acc aag agc agg act cgc tac gtc    1210
Gly Gly His Cys Gly Arg Leu Gly Thr Lys Ser Arg Thr Arg Tyr Val
290                 295                 300                 305 cgg gtc cag ccc gcc aac aac ggg agc ccc tgc ccc gag ctc gaa gaa    1258
Arg Val Gln Pro Ala Asn Asn Gly Ser Pro Cys Pro Glu Leu Glu Glu
                310                 315                 320 gag gct gag tgc gtc cct gat aac tgc gtc taa gaccagagcc ccgcagcccc   1311
Glu Ala Glu Cys Val Pro Asp Asn Cys Val
                325                 330 tggggccccc cggagccatg gggtgtcggg ggctcctgtg caggctcatg ctgcaggcgg   1371
ccgagggcac agggggtttc gcgctgctcc tgaccgcggt gaggccgcgc cgaccatctc   1431
tgcactgaag ggccctctgg tggccggcac gggcattggg aaacagcctc ctcctttccc   1491
aaccttgctt cttagggggcc cccgtgtccc gtctgctctc agcctcctcc tcctgcagga   1551
taaagtcatc cccaaggctc cagctactct aaattatgtc tccttataag ttattgctgc   1611
tccaggagat tgtccttcat cgtccagggg cctggctccc acgtggttgc agatacctca   1671
gacctggtgc tctaggctgt gctgagccca ctctcccgag ggcgcatcca agcgggggcc   1731
acttgagaag tgaataaatg gggcggtttc ggaagcgtca aaaaaaaaaa aaaa          1785

<210> SEQ ID NO 2
<211> LENGTH: 331
<212> TYPE: PRT
<213> ORGANISM: Homo sapiens

<400> SEQUENCE: 2

Met Glu Asn Pro Ser Pro Ala Ala Ala Leu Gly Lys Ala Leu Cys Ala
1               5                   10                  15

Leu Leu Leu Ala Thr Leu Gly Ala Ala Gly Gln Pro Leu Gly Gly Glu
            20                  25                  30

Ser Ile Cys Ser Ala Gly Ala Pro Ala Lys Tyr Ser Ile Thr Phe Thr
        35                  40                  45

Gly Lys Trp Ser Gln Thr Ala Phe Pro Lys Gln Tyr Pro Leu Phe Arg
    50                  55                  60

Pro Pro Ala Gln Trp Ser Ser Leu Leu Gly Ala Ala His Ser Ser Asp
65                  70                  75                  80

Tyr Ser Met Trp Arg Lys Asn Gln Tyr Val Ser Asn Gly Leu Arg Asp
                85                  90                  95

Phe Ala Glu Arg Gly Glu Ala Trp Ala Leu Met Lys Glu Ile Glu Ala
            100                 105                 110

Ala Gly Glu Ala Leu Gln Ser Val His Ala Val Phe Ser Ala Pro Ala
        115                 120                 125

Val Pro Ser Gly Thr Gly Gln Thr Ser Ala Glu Leu Glu Val Gln Arg
    130                 135                 140

Arg His Ser Leu Val Ser Phe Val Val Arg Ile Val Pro Ser Pro Asp
145                 150                 155                 160

Trp Phe Val Gly Val Asp Ser Leu Asp Leu Cys Asp Gly Asp Arg Trp
                165                 170                 175

Arg Glu Gln Ala Ala Leu Asp Leu Tyr Pro Tyr Asp Ala Gly Thr Asp
            180                 185                 190

Ser Gly Phe Thr Phe Ser Ser Pro Asn Phe Ala Thr Ile Pro Gln Asp
        195                 200                 205
```

-continued

```
Thr Val Thr Glu Ile Thr Ser Ser Pro Ser His Pro Ala Asn Ser
    210                 215                 220

Phe Tyr Tyr Pro Arg Leu Lys Ala Leu Pro Pro Ile Ala Arg Val Thr
225                 230                 235                 240

Leu Val Arg Leu Arg Gln Ser Pro Arg Ala Phe Ile Pro Pro Ala Pro
                245                 250                 255

Val Leu Pro Ser Arg Asp Asn Glu Ile Val Asp Ser Ala Ser Val Pro
                260                 265                 270

Glu Thr Pro Leu Asp Cys Glu Val Ser Leu Trp Ser Ser Trp Gly Leu
            275                 280                 285

Cys Gly Gly His Cys Gly Arg Leu Gly Thr Lys Ser Arg Thr Arg Tyr
    290                 295                 300

Val Arg Val Gln Pro Ala Asn Asn Gly Ser Pro Cys Pro Glu Leu Glu
305                 310                 315                 320

Glu Glu Ala Glu Cys Val Pro Asp Asn Cys Val
                325                 330

<210> SEQ ID NO 3
<211> LENGTH: 19
<212> TYPE: DNA
<213> ORGANISM: Artificial
<220> FEATURE:
<223> OTHER INFORMATION: primer

<400> SEQUENCE: 3
cgcgcatagc tccgactac                                                    19

<210> SEQ ID NO 4
<211> LENGTH: 15
<212> TYPE: DNA
<213> ORGANISM: Artificial
<220> FEATURE:
<223> OTHER INFORMATION: primer

<400> SEQUENCE: 4
gccgcgtccg caaag                                                        15

<210> SEQ ID NO 5
<211> LENGTH: 30
<212> TYPE: DNA
<213> ORGANISM: Artificial
<220> FEATURE:
<223> OTHER INFORMATION: probe

<400> SEQUENCE: 5
aggaagaacc agtacgtcag taacgggctg                                        30

<210> SEQ ID NO 6
<211> LENGTH: 36
<212> TYPE: DNA
<213> ORGANISM: Artificial
<220> FEATURE:
<223> OTHER INFORMATION: primer

<400> SEQUENCE: 6
tccctctaga gccaccatgg aaaaccccag cccggc                                 36

<210> SEQ ID NO 7
<211> LENGTH: 35
<212> TYPE: DNA
<213> ORGANISM: Artificial
<220> FEATURE:
<223> OTHER INFORMATION: primer2
```

<400> SEQUENCE: 7
aaggcatcac gtgttagacg cagttatcag ggacg                                      35

<210> SEQ ID NO 8
<211> LENGTH: 19
<212> TYPE: PRT
<213> ORGANISM: Homo sapiens

<400> SEQUENCE: 8

Pro Leu Gly Gly Glu Ser Ile Cys Ser Ala Gly Ala Pro Ala Lys Tyr
1               5                   10                  15

Ser Ile Thr

<210> SEQ ID NO 9
<211> LENGTH: 19
<212> TYPE: PRT
<213> ORGANISM: Homo sapiens

<400> SEQUENCE: 9

Thr Phe Thr Gly Lys Trp Ser Gln Thr Ala Phe Pro Lys Gln Tyr Pro
1               5                   10                  15

Leu Phe Arg

<210> SEQ ID NO 10
<211> LENGTH: 15
<212> TYPE: PRT
<213> ORGANISM: Homo sapiens

<400> SEQUENCE: 10

His Ser Ser Asp Tyr Ser Met Trp Arg Lys Asn Gln Tyr Val Ser
1               5                   10                  15

<210> SEQ ID NO 11
<211> LENGTH: 23
<212> TYPE: PRT
<213> ORGANISM: Homo sapiens

<400> SEQUENCE: 11

Asp Ala Gly Thr Asp Ser Gly Phe Thr Phe Ser Ser Pro His Phe Ala
1               5                   10                  15

Thr Ile Pro Gln Asp Thr Val
            20

<210> SEQ ID NO 12
<211> LENGTH: 12
<212> TYPE: PRT
<213> ORGANISM: Homo sapiens

<400> SEQUENCE: 12

Asn Glu Ile Val Asp Ser Ala Ser Val Pro Glu Thr
1               5                   10

<210> SEQ ID NO 13
<211> LENGTH: 330
<212> TYPE: PRT
<213> ORGANISM: Rattus norvegicus

<400> SEQUENCE: 13

Met Glu Asn Val Ser Phe Ser Leu Asp Arg Thr Leu Trp Val Phe Leu
1               5                   10                  15

Leu Ala Met Leu Gly Ser Thr Ala Gly Gln Pro Leu Gly Gly Glu Ser
            20                  25                  30

Val Cys Thr Ala Arg Pro Leu Ala Arg Tyr Ser Ile Thr Phe Thr Gly
         35                  40                  45

Lys Trp Ser Gln Thr Ala Phe Pro Lys Gln Tyr Pro Leu Phe Arg Pro
 50                  55                  60

Pro Ala Gln Trp Ser Ser Leu Leu Gly Ala Ala His Ser Ser Asp Tyr
 65                  70                  75                  80

Ser Met Trp Arg Lys Asn Glu Tyr Val Ser Asn Gly Leu Arg Asp Phe
                 85                  90                  95

Ala Glu Arg Gly Glu Ala Trp Ala Leu Met Lys Glu Ile Glu Ala Ala
                100                 105                 110

Gly Glu Lys Leu Gln Ser Val His Ala Val Phe Ser Ala Pro Ala Val
                115                 120                 125

Pro Ser Gly Thr Gly Gln Thr Ser Ala Glu Leu Glu Val His Pro Arg
130                 135                 140

His Ser Leu Val Ser Phe Val Val Arg Ile Val Pro Ser Pro Asp Trp
145                 150                 155                 160

Phe Val Gly Ile Asp Ser Leu Asp Leu Cys Glu Gly Arg Trp Lys
                165                 170                 175

Glu Gln Val Val Leu Asp Leu Tyr Pro His Asp Ala Gly Thr Asp Ser
                180                 185                 190

Gly Phe Thr Phe Ser Ser Pro Asn Phe Ala Thr Ile Pro Gln Asp Thr
                195                 200                 205

Val Thr Glu Ile Thr Ala Ser Ser Pro Ser His Pro Ala Asn Ser Phe
                210                 215                 220

Tyr Tyr Pro Arg Leu Lys Ser Leu Pro Pro Ile Ala Lys Val Thr Phe
225                 230                 235                 240

Val Arg Leu Arg Gln Ser Pro Arg Ala Phe Ala Pro Pro Ser Leu Asp
                245                 250                 255

Leu Ala Ser Arg Gly Asn Glu Ile Val Asp Ser Leu Ser Val Pro Glu
                260                 265                 270

Thr Pro Leu Asp Cys Glu Val Ser Leu Trp Ser Ser Trp Gly Leu Cys
                275                 280                 285

Gly Gly Pro Cys Gly Lys Leu Gly Ala Lys Ser Arg Thr Arg Tyr Val
290                 295                 300

Arg Val Gln Pro Ala Asn Asn Gly Thr Pro Cys Pro Glu Leu Glu Glu
305                 310                 315                 320

Glu Ala Glu Cys Ala Pro Asp Asn Cys Val
                325                 330

<210> SEQ ID NO 14
<211> LENGTH: 34
<212> TYPE: DNA
<213> ORGANISM: Artificial
<220> FEATURE:
<223> OTHER INFORMATION: primer

<400> SEQUENCE: 14
ggggaggctt ggtacaacct gggggtccc tgag                              34

<210> SEQ ID NO 15
<211> LENGTH: 45
<212> TYPE: DNA
<213> ORGANISM: Artificial
<220> FEATURE:
<223> OTHER INFORMATION: primer

<400> SEQUENCE: 15
gaacagcctg agagccgagg acacggctgt gtattactgt gcaag                45

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
gggaagcttg ccaccatgga aaccccagcg                                 30

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
cagtcgtacg tttgatctcc accttggtcc                                 30

<210> SEQ ID NO 18
<211> LENGTH: 31
<212> TYPE: DNA
<213> ORGANISM: Artificial
<220> FEATURE:
<223> OTHER INFORMATION: primer

<400> SEQUENCE: 18
gcggccgcca ccatggagtt tgtgctgagc t                               31

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
accgatgggc ccttggtgga                                            20

<210> SEQ ID NO 20
<211> LENGTH: 381
<212> TYPE: DNA
<213> ORGANISM: Homo sapiens

<400> SEQUENCE: 20
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttagc agcagctact tagcctggta ccagcagaaa   180
cctggccagg ctcccaggct cctcatctat ggtgcatcca gcagggccac tggcatccca   240
gacaggttca gtggcagtgg gtctgggaca gacttcactc tcaccatcag cagactggag   300
cctgaagatt ttgcagtgta ttactgtcag cagtatagta gctcgctcac tttcggcggg   360
gggaccaagg tggagatcaa a                                            381

<210> SEQ ID NO 21
<211> LENGTH: 441
<212> TYPE: DNA
<213> ORGANISM: Homo sapiens

```
<400> SEQUENCE: 21
atggagtttg tgctgagctg ggttttcctt gttgctatat taaaaggtgt ccagtgtgag    60
gttcagctgg tgcagtctgg gggaggcttg gtacatcctg gggggtccct gagactctcc   120
tgtgcaggct ctggattcac cttcagtagc tatgttatgc actggcttcg ccaggctcca   180
ggaaaaggtc tggagtgggt atcagttatt ggtactggtg gtgtcacaca ctatgcagac   240
tccgtgaagg gccgattcac catctccaga gacaatgcca agaactcctt gtatcttcaa   300
atgaacagcc tgagagccga ggacatggct atgtattact gtgcaagatg gggttactat   360
ggttcgggga gttatgagaa tgatgctttt gatatctggg gccaagggac aatggtcacc   420
gtctcttcag cctccaccaa g                                             441

<210> SEQ ID NO 22
<211> LENGTH: 441
<212> TYPE: DNA
<213> ORGANISM: Homo sapiens

<400> SEQUENCE: 22
atggagtttg tgctgagctg ggttttcctt gttgctatat taaaaggtgt ccagtgtgag    60
gttcagctgg tgcagtctgg gggaggcttg gtacaacctg gggggtccct gagactctcc   120
tgtgcaggct ctggattcac cttcagtagc tatgttatgc actggcttcg ccaggctcca   180
ggaaaaggtc tggagtgggt atcagttatt ggtactggtg gtgtcacaca ctatgcagac   240
tccgtgaagg gccgattcac catctccaga gacaatgcca agaactcctt gtatcttcaa   300
atgaacagcc tgagagccga ggacacggct gtgtattact gtgcaagatg gggttactat   360
ggttcgggga gttatgagaa tgatgctttt gatatctggg gccaagggac aatggtcacc   420
gtctcttcag cctccaccaa g                                             441

<210> SEQ ID NO 23
<211> LENGTH: 381
<212> TYPE: DNA
<213> ORGANISM: Homo sapiens

<400> SEQUENCE: 23
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttagc agcagctact tagcctggta ccagcagaaa   180
cctggccagg ctcccaggct cctcatctat ggtgcatcca gcagggccac tggcatccca   240
gacaggttca gtggcagtgg gtctgggaca gacttcactc tcaccatcag cagactggag   300
cctgaagatt ttgcagtgta ttactgtcag cagtatggta gctcactcac tttcggcgga   360
gggaccaagg tggagatcaa a                                             381

<210> SEQ ID NO 24
<211> LENGTH: 423
<212> TYPE: DNA
<213> ORGANISM: Homo sapiens

<400> SEQUENCE: 24
atggagtttg tgctgagctg ggttttcctt gttgctatat taaaaggtgt ccagtgtgag    60
gttcagctgg tgcagtctgg gggaggcttg gtacatcctg gggggtccct gagactctcc   120
tgtgcaggct ctggattcac cttcagtagc tatgttcatgc actgggttcg ccaggctcca   180
ggaaaaggtc tggagtgggt atcagtaatt ggtactggtg gtgtcacaaa ctatgcagac   240
```

```
tccgtgaagg gccgattcac catctccaga gacaatgcca agaactccct gtatcttcaa      300
atgaacagcc tgagagccga ggacatggct gtgtattact gtgcaagatg gggggactgg      360
gatgatgctt ttgatatctg gggccaaggg acaatggtca ccgtctcttc agcctccacc      420
aag                                                                    423
```

<210> SEQ ID NO 25
<211> LENGTH: 423
<212> TYPE: DNA
<213> ORGANISM: Homo sapiens

<400> SEQUENCE: 25

```
atggagtttg tgctgagctg ggttttcctt gttgctatat taaaaggtgt ccagtgtgag      60
gttcagctgg tgcagtctgg gggaggcttg gtacaacctg gggggtccct gagactctcc      120
tgtgcaggct ctggattcac cttcagtagc tatgtcatgc actgggttcg ccaggctcca      180
ggaaaaggtc tggagtgggt atcagtaatt ggtactggtg gtgtcacaaa ctatgcagac      240
tccgtgaagg gccgattcac catctccaga gacaatgcca agaactccct gtatcttcaa      300
atgaacagcc tgagagccga ggacacggct gtgtattact gtgcaagatg gggggactgg      360
gatgatgctt ttgatatctg gggccaaggg acaatggtca ccgtctcttc agcctccacc      420
aag                                                                    423
```

<210> SEQ ID NO 26
<211> LENGTH: 127
<212> TYPE: PRT
<213> ORGANISM: Homo sapiens

<400> SEQUENCE: 26

Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Ser Ser Ser Leu Thr Phe Gly Gly Gly Thr Lys Val Glu Ile Lys
        115                 120                 125

<210> SEQ ID NO 27
<211> LENGTH: 147
<212> TYPE: PRT
<213> ORGANISM: Homo sapiens

<400> SEQUENCE: 27

Met Glu Phe Val Leu Ser Trp Val Phe Leu Val Ala Ile Leu Lys Gly
1               5                   10                  15

Val Gln Cys Glu Val Gln Leu Val Gln Ser Gly Gly Gly Leu Val Met
            20                  25                  30

```
Pro Gly Gly Ser Leu Arg Leu Ser Cys Ala Gly Ser Gly Phe Thr Phe
        35                  40                  45

Ser Ser Tyr Val Met His Trp Leu Arg Gln Ala Pro Gly Lys Gly Leu
    50                  55                  60

Glu Trp Val Ser Val Ile Gly Thr Gly Gly Val Thr His Tyr Ala Asp
65                  70                  75                  80

Ser Val Lys Gly Arg Phe Met Ile Ser Arg Asp Asn Ala Lys Asn Ser
                85                  90                  95

Leu Tyr Leu Gln Met Asn Ser Leu Arg Ala Glu Asp Thr Ala Met Tyr
            100                 105                 110

Tyr Cys Ala Arg Trp Gly Tyr Gly Ser Gly Ser Tyr Glu Asn Asp
        115                 120                 125

Ala Phe Asp Ile Trp Gly Gln Gly Thr Met Val Thr Val Ser Ser Ala
        130                 135                 140

Ser Thr Lys
145

<210> SEQ ID NO 28
<211> LENGTH: 147
<212> TYPE: PRT
<213> ORGANISM: Homo sapiens

<400> SEQUENCE: 28

Met Glu Phe Val Leu Ser Trp Val Phe Leu Val Ala Ile Leu Lys Gly
1               5                   10                  15

Val Gln Cys Glu Val Gln Leu Val Gln Ser Gly Gly Gly Leu Val Gln
            20                  25                  30

Pro Gly Gly Ser Leu Arg Leu Ser Cys Ala Gly Ser Gly Phe Thr Phe
        35                  40                  45

Ser Ser Tyr Val Met His Trp Leu Arg Gln Ala Pro Gly Lys Gly Leu
    50                  55                  60

Glu Trp Val Ser Val Ile Gly Thr Gly Gly Val Thr His Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Trp Gly Tyr Gly Ser Gly Ser Tyr Glu Asn Asp
        115                 120                 125

Ala Phe Asp Ile Trp Gly Gln Gly Thr Met Val Thr Val Ser Ser Ala
        130                 135                 140

Ser Thr Lys
145

<210> SEQ ID NO 29
<211> LENGTH: 127
<212> TYPE: PRT
<213> ORGANISM: Homo sapiens

<400> SEQUENCE: 29

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45
```

Val Ser Ser Tyr Leu Ala Trp Tyr Gln Gln Lys Pro Gly Gln Ala
 50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
             100                 105                 110

Gly Ser Ser Leu Thr Phe Gly Gly Gly Thr Lys Val Glu Ile Lys
         115                 120                 125

<210> SEQ ID NO 30
<211> LENGTH: 141
<212> TYPE: PRT
<213> ORGANISM: Homo sapiens

<400> SEQUENCE: 30

Met Glu Phe Val Leu Ser Trp Val Phe Leu Val Ala Ile Leu Lys Gly
 1               5                  10                  15

Val Gln Cys Glu Val Gln Leu Val Gln Ser Gly Gly Gly Leu Val Met
             20                  25                  30

Pro Gly Gly Ser Leu Arg Leu Ser Cys Ala Gly Ser Gly Phe Thr Phe
         35                  40                  45

Ser Ser Tyr Val Met His Trp Val Arg Gln Ala Pro Gly Lys Gly Leu
 50                  55                  60

Glu Trp Val Ser Val Ile Gly Thr Gly Gly Val Thr Asn Tyr Ala Asp
 65                  70                  75                  80

Ser Val Lys Gly Arg Phe Met Ile Ser Arg Asp Asn Ala Lys Asn Ser
                 85                  90                  95

Leu Tyr Leu Gln Met Asn Ser Leu Arg Ala Glu Asp Thr Ala Val Tyr
             100                 105                 110

Tyr Cys Ala Arg Trp Gly Asp Trp Asp Ala Phe Asp Ile Trp Gly
         115                 120                 125

Gln Gly Thr Met Val Thr Val Ser Ser Ala Ser Thr Lys
 130                 135                 140

<210> SEQ ID NO 31
<211> LENGTH: 141
<212> TYPE: PRT
<213> ORGANISM: Homo sapiens

<400> SEQUENCE: 31

Met Glu Phe Val Leu Ser Trp Val Phe Leu Val Ala Ile Leu Lys Gly
 1               5                  10                  15

Val Gln Cys Glu Val Gln Leu Val Gln Ser Gly Gly Gly Leu Val Gln
             20                  25                  30

Pro Gly Gly Ser Leu Arg Leu Ser Cys Ala Gly Ser Gly Phe Thr Phe
         35                  40                  45

Ser Ser Tyr Val Met His Trp Val Arg Gln Ala Pro Gly Lys Gly Leu
 50                  55                  60

Glu Trp Val Ser Val Ile Gly Thr Gly Gly Val Thr Asn Tyr Ala Asp
 65                  70                  75                  80

Ser Val Lys Gly Arg Phe Thr Ile Ser Arg Asp Asn Ala Lys Asn Ser
                 85                  90                  95

Leu Tyr Leu Gln Met Asn Ser Leu Arg Ala Glu Asp Thr Ala Val Tyr
             100                 105                 110

-continued

```
Tyr Cys Ala Arg Trp Gly Asp Trp Asp Asp Ala Phe Asp Ile Trp Gly
        115                 120                 125

Gln Gly Thr Met Val Thr Val Ser Ser Ala Ser Thr Lys
    130                 135                 140
```

RG1 ANTIBODIES AND USES THEREOF

This application is a divisional application of U.S. Ser. No. 10/895,183, filed Jul. 20, 2004, now U.S. Pat. No. 7,335,748, issued on Feb. 26, 2008, which claims the benefit of U.S. Provisional Application Ser. No. 60/489,032, filed on Jul. 22, 2003, which is incorporated herein by reference.

FIELD OF THE INVENTION

This invention relates to novel antibodies directed against a polypeptide, RG1, which is preferentially expressed in prostate and other tumor cells. In particular, the invention relates to the use of these antibodies for the treatment and detection of cancer and cancer metastasis.

BACKGROUND OF THE INVENTION

Prostate cancer is a frequently occurring disease in man, in that it is found in about one third of men over the age of 45. There is evidence for both genetic and environmental causes, with the majority of cases probably being the result of a combination of both factors. Studies of familial cancer have suggested that genetic predisposition plays a role in about 5-10% of all prostate cancers, and in about 45% of cases in men younger than 55.

There is evidence that prostate cancer develops as a multi-step disease, with one of the precursor lesions being prostatic intraepithelial neoplasia (PIN). Early stages of the disease are androgen dependent, while later stages are hormone independent. A proliferative disorder of the prostate known as benign prostatic hyperplasia is often detected clinically but is probably not a stage in the development of cancer. It is, however, frequently associated with prostate cancer. Cancers in the prostate are often multifocal, generally slow growing, and heterogeneous. Late stage cancers frequently metastasize to the lymph nodes and to the bone.

Prostate cancer is usually diagnosed by physical examination and by serum levels of prostate specific antigen (PSA). Radical prostatectomy is the treatment of choice for localized disease. Advanced metastatic disease is treated currently by androgen ablation induced by orchiectomy or treatment with GnRH (gonadotrophin releasing hormone), and by anti-androgen therapy. However, advanced disease almost invariably becomes hormone resistant and there is no cure for progressive disease. Moreover, there are serious side effects associated with both radical prostatectomy and androgen ablation therapy. These include a high risk of incontinence and impotence associated with radical prostatectomy and bone fractures and osteoporosis associated with androgen ablation therapy.

There is, therefore, a considerable need for new therapeutic approaches for both early and late stage prostate cancer. There is also a significant need for new diagnostic agents, as this significantly influences the treatment options. For example, if disease has progressed beyond the prostate and has metastasized to the lymph nodes, radical prostatectomy is not undertaken as it has no effect on progression, but may have significant unwanted side effects. An agent that could detect metastasis, in vivo, would have considerable value.

Changes in the expression of specific proteins have been demonstrated in prostate cancer including abnormal p53 expression in late stage prostate cancer, reduced levels of TGF-β receptors, reduced levels of E-cadherin, C-Cam (a cell adhesion molecule), and several integrins. The expression of the oncogene bcl-2 is strikingly elevated in late stage androgen independent tumors, and prognosis for patients expression bcl-2 at elevated levels is relatively poor. While the previously mentioned changes in gene expression are well documented, no changes in expression have been identified that have been demonstrated to be causative for the disease. It would, therefore, be useful to identify new proteins whose expression is linked to the presence or development of prostate tumors that could serve as molecular targets for compositions directed to prostate cancer diagnosis and therapy.

The polypeptide RG1 (see U.S. Pat. No. 5,871,969) is a homolog of the Mindin/F-spondin family, which are extracellular matrix proteins. The RG1 polypeptide was demonstrated to be highly expressed in prostate tissue (see WO98/45442), and should be a useful target for diagnosis and therapy of prostate cancer, as well as in other cancers where it is expressed.

SUMMARY OF THE INVENTION

The present invention provides antibodies, or antigen-binding antibody fragments thereof, or variants thereof, that are highly selective for RG1 polypeptides, and which may be employed in methods for detection of RG1 expression, which is associated with disease states such as cancer of the prostate, kidney, colon or ovaries, and in the treatment of such disease states.

Toward these ends, it is an object of the invention to provide isolated antibodies, or antigen-binding antibody fragments thereof, or variants thereof, that specifically bind to an epitope present in an RG1 polypeptide (SEQ ID NO: 2). Particularly preferred are human antibodies that bind to epitope of the RG1 polypeptide with a dissociation constant ($K_D$) which is less than or equal to 1 µM, more preferably less than or equal to 100 nM and most preferably less than or equal to 10 nM.

In accordance with further preferred embodiments of the invention, isolated antibodies and antigen-binding antibody fragments thereof, comprising a light chain variable region comprising the amino acid sequences of SEQ ID NO: 26 or SEQ ID NO: 29 are provided.

Also provided are isolated antibodies and antigen-binding antibody fragments thereof, comprising a heavy chain variable region comprising the amino acid sequences SEQ ID NO: 27, SEQ ID NO: 28, SEQ ID NO: 30 or SEQ ID NO: 31. A particularly preferred embodiment is a human antibody, comprising a light chain variable region having the amino acid sequence SEQ ID NO: 26 and a heavy chain variable region having the amino acid sequence SEQ ID NO: 27 or SEQ ID NO: 28. A second particularly preferred embodiment is a human antibody, comprising a light chain variable region having the amino acid sequence SEQ ID NO: 29 and a heavy chain variable region having the amino acid sequence SEQ ID NO: 30 or SEQ ID NO: 31.

In a further aspect of the invention, light chain variable regions and heavy chain variable regions with amino acid sequences having 80% sequence identity to the amino acid sequences described above are also contemplated.

Also provided are nucleotide sequences which encode the light chain and heavy chain variable regions of the antibodies described above. Preferred is an antibody comprising a light chain variable region encoded by a nucleotide sequence comprising SEQ ID NO: 20 or SEQ ID NO: 23. Also preferred is an antibody comprising a heavy chain variable region encoded by a nucleotide sequence comprising SEQ ID NO: 21, SEQ ID NO: 22, SEQ ID NO: 24, or SEQ ID NO: 25.

In accordance with certain preferred embodiments of this aspect of the invention, the antibodies are conjugated to a detectable marker, for use as a diagnostic agent for administration to cells in vitro, to cells ex vivo and to cells in vivo, or to a multicellular organism. Particularly preferred would be an antibody conjugated to a radiolabel, an enzyme, a chromophore or a fluorescer. Particularly preferred methods of detection are immunoscintigraphy and positron emitting tomography, in which the antibody would be conjugated to a radioiotope such as $^{111}$In or $^{99m}$Tc, for immunoscintigraphy, or to $^{43}$Sc, $^{44}$Sc, $^{52}$Fe, $^{55}$Co, $^{68}$Ga, $^{64}$Cu, $^{86}$Y or $^{94m}$Tc, for positron emitting tomography.

In a further aspect of the invention there are provided antibodies that are conjugated to a therapeutic agent, e.g. ricin or a radioisotope, for administration to cells in vitro, to cells ex vivo and to cells in vivo, or to a multicellular organism. Preferred in this regard are therapeutic agents that are cytotoxic. Particularly preferred for a therapeutic agent would be antibodies conjugated to a radioisotope, such as $^{90}$Y and $^{177}$Lu. In certain preferred embodiments in this regard is administration of such conjugated antibodies to a human patient for treatment of a disease state characterized by RG1 expression, such as prostate cancer, and in particular, advanced metastatic prostate cancer.

In a further aspect of the invention, conjugation of an RG1 antibody, or antigen-binding fragment thereof, to a detectable marker or cytotoxic agent is accomplished through use of a chelator selected from the group consisting of p-SCN-Benzyl-DTPA and derivatives thereof, 1,4,7,10-tetraazacyclododecane-N,N', N'',N'''-tetracetic acid (DOTA) and derivatives thereof, and 1,4,7-triazacyclononane-N,N',N''-triacetic acid (NOTA) and derivatives thereof.

In a further aspect of the invention is a method for treatment of a disease-state associated with expression of an RG1 polypeptide, such as prostate, which uses the immunoconjugates of the present invention.

In a further aspect of the invention is a method for detection of a disease-state associated with expression of an RG1 polypeptide, such as prostate cancer, which uses the immunoconjugates of the present invention.

In a further aspect of the invention, peptides and anti-idiotypic antibodies are provided which can be used to stimulate an immune response.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIG. 3: Amino acid sequence of the variable chain regions of human monoclonal antibody B, including a mutated variable heavy chain region. V$_L$ (SEQ ID NO: 26), V$_H$ (SEQ ID NO: 27), B_3M, V$_H$ (SEQ ID NO: 28).

FIG. 4: Amino acid sequence of the variable chain regions of human monoclonal antibody C, including a mutated variable heavy chain region. V$_L$ (SEQ ID NO: 29), V$_H$ (SEQ ID NO: 30), C_2 m, V$_H$ (SEQ ID NO: 31).

DETAILED DESCRIPTION OF THE INVENTION

Definitions

Figure 1:
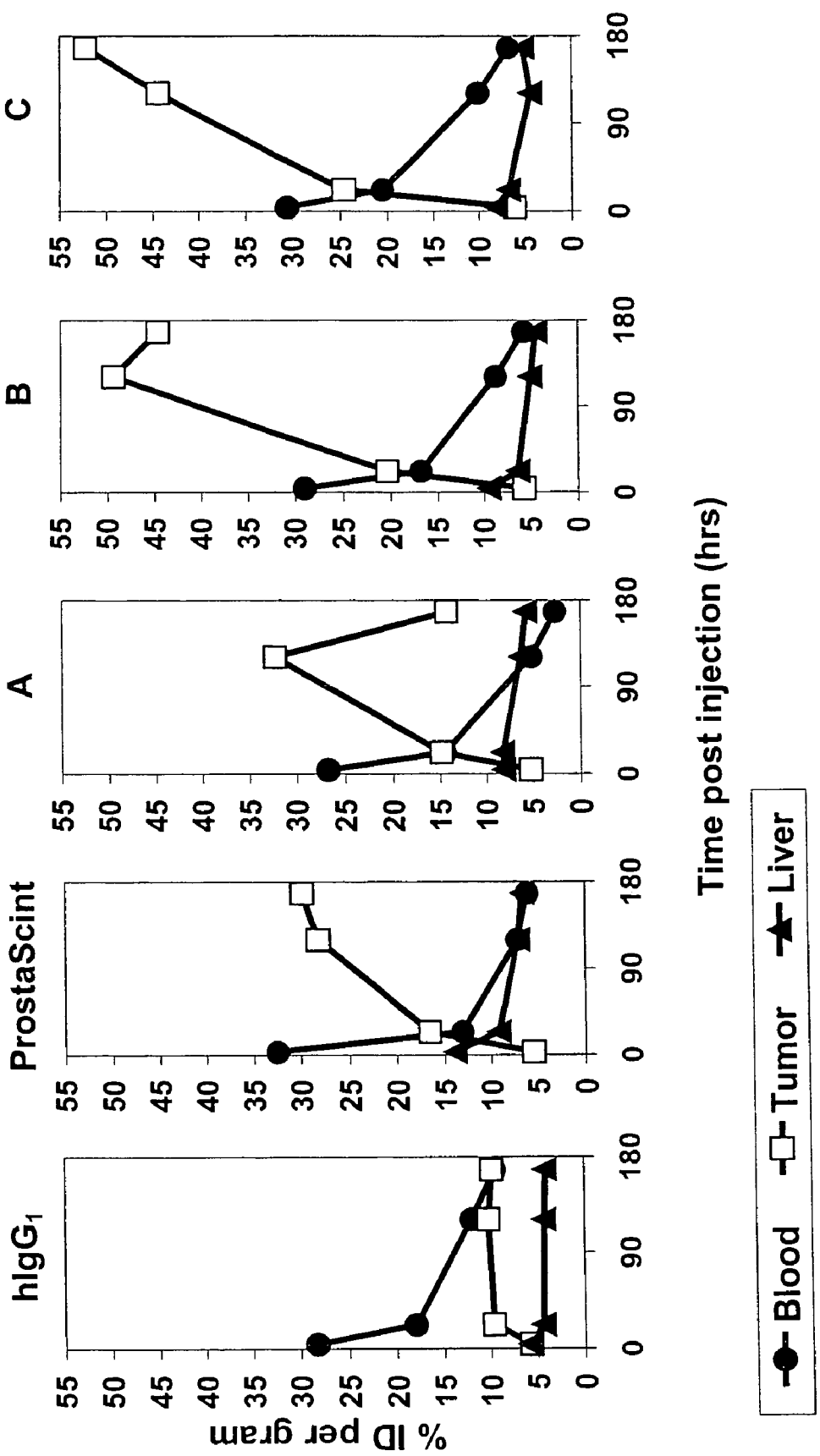
FIG. 1: Biodistribution of $^{111}$In labeled RG1 Antibodies: Three RG1 antibodies (A, B, and C), a non-specific hIgG, control antibody, and the antibody CYT-356 (PROSTASCINT™, Cytogen Corporation. Princeton N.J.) were radiolabeled with $^{111}$In. Radiolabeled antibodies (specific activity: 0:3 mCi/mg) were administered i.v. into tumor (LNCaP) bearing nude mice. Twelve animals per group (3 animals per time point) were sacrificed at 6, 24, 120, and 150 hr p.i. and the accumulation in the tumor, blood and liver monitored. (See Example 11)

As used in the specification, examples and appended claims, unless specified to the contrary, the following terms have the meaning indicated.

"rg1" refers to the polynucleotide having the sequence set out in SEQ ID NO: 1 and polynucleotides encoding polypeptides having the amino acid sequence of RG1 set out in SEQ ID NO: 2; and to polynucleotides encoding RG1 variants, derivatives and fragments, and fragments of the variants and derivatives. Rg1 also refers to such polynucleotides composed of RNA as well as to polynucleotides which are the complement of polynucleotides which encode the polypeptide sequence set out in SEQ ID NO: 2.

"RG1" refers to tile polypeptide having the amino acid sequence set out in SEQ ID NO: 2, variants and derivatives thereof, and fragments of SEQ ID NO: 2, variants and derivatives thereof. The terms "variant", "fragment" and "derivative", when referring to the polypeptide of SEQ ID NO: 2 mean a polypeptide which retains essentially the same biologic and/or immunologic activity as the polypeptide of SEQ ID NO: 2.

"Biologic activity" refers to the structural, regulatory or biochemical functions of naturally occurring RG1 polypeptide.

"Immunologic activity" refers to (1) the capability of the natural, recombinant or synthetic RG1, or any fragment thereof, to induce a specific immune response in appropriate animals or cells and to bind with specific antibodies, or (2) the capacity of antibodies to RG1 to bind RG1 in vivo and trigger an enhanced, cellular immune response to RG1 expressing tissue or tumor.

"Naturally occurring RG1" refers to RG1 produced by human cells that have not been genetically engineered and specifically contemplates various RG1 forms arising from post-translational modifications of the polypeptide including but not limited to acetylation, carboxylation, glycosylation, phosphorylation, lipidation, acylation, and cleavage.

"Native RG1" or "nRG1" refers to RG1 which is in its native conformation.

"Polynucleotide(s)" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term "polynucleotide" includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritium-labelled bases, to name just two examples, are polynucleotides as the term is used herein.

It will be appreciated that a great variety of modifications have been made to DNA and RNA that serve many useful purposes known to those of skill in the art. The term "polynucleotide" as it is employed herein embraces such chemically, enzymatically or metabolically modified forms of polynucleotides, as well as the chemical forms of DNA and RNA characteristic of viruses and cells, including simple and complex cells, inter alia.

"Oligonucleotide(s)" refers to relatively short polynucleotides. Often the term refers to single-stranded deoxyribonucleotides, but it can refer as well to single- or double-stranded ribonucleotides, RNA:DNA hybrids and double-stranded DNAs, among others. Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms. "Oligonucleotides" or "oligomers" or polynucleotide "fragment", "portion", or "segment" refers to a polynucleotide sequence of at least about 10 nucleotides and as many as about 60 nucleotides, preferably about 15 to 30 nucleotides, and more preferably about 20-25 nucleotides.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids at commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Common modifications include glycosylation, lipid attachment, sulfation, gamma-carboxylation of glutamic acid residues, hydroxylation and ADP-ribosylation, and these and others are described in most basic texts, such as, for instance, I. E. Creighton, *Proteins—Structure and Molecular Properties,* 2nd Ed., W. H. Freeman and Company, New York, 1993. Many detailed reviews are available on this subject, such as, for example, those provided by Wold, F., in *Posttranslational Covalent Modification of Proteins,* B. C. Johnson, Ed., Academic Press, New York, pp 1-12, 1983; Seifter et al., *Meth. Enzymol.* 182: 626-646, 1990 and Rattan et al., *Protein Synthesis: Posttranslational Modifications and Aging,* Ann. N.Y. Acad. Sci. 663: 48-62, 1992.

It will be appreciated, as is well known, and as noted above, that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally. Circular, branched and branched circular polypeptides may be synthesized by non-translational natural processes and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli,* prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli.* Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation, inter alia. Similar considerations apply to other modifications.

In general, as used herein, the term polypeptide encompasses all such modifications, particularly those that are present in polypeptides synthesized by expressing a polynucleotide in a host cell.

"Derivative" refers to polynucleotides or polypeptides derived from naturally occurring rg1, RG1, or from antibodies binding RG1, respectively, by chemical modifications such as ubiquitination, labeling (e.g., with radionuclides, various enzymatic modifications), pegylation (derivatization with polyethylene glycol) or by insertion or substitution of amino acids such as ornithine (or substitution of the nucleotides which code for such as an amino acid), which do not normally occur in human proteins.

"Polynucleotide encoding a polypeptide" as used herein encompasses polynucleotides which include a sequence encoding a polypeptide of the present invention, particularly the RG1 polypeptide having the amino acid sequence set out in SEQ ID NO: 2. The term encompasses polynucleotides that include a single continuous region or discontinuous regions encoding the polypeptide (for example, interrupted by introns) together with additional regions.

A polypeptide "fragment", "portion", or "segment" is a stretch of amino acid residues of at least about 5 amino acids, often at least about 7 amino acids, typically at least about 9 to 13 amino acids, and in various embodiments, at least about 17 or more amino acids. "Fragment" refers to a polypeptide having an amino acid sequence that is entirely the same as part, but not all, of the amino acid sequence of the aforementioned RG1 polypeptides, or antibodies to RG1, and variants or derivatives thereof.

"Deletion" is defined as a change in either polynucleotide or amino acid sequences in which one or more polynucleotides or amino acid residues, respectively, are absent.

"Insertion" or "addition" is that change in a polynucleotide or amino acid sequence which has resulted in the addition of one or more polynucleotides or amino acid residues, respectively, as compared to the naturally occurring polynucleotide or amino acid sequence.

"Substitution" results from the replacement of one or more polynucleotides or amino acids by different polynucleotides or amino acids, respectively.

"Variant(s)" of polynucleotides or polypeptides, as the term is used herein, are described below and elsewhere in the present disclosure in greater detail.

A variant of a polynucleotide is a polynucleotide that differs in polynucleotide sequence from another, reference polynucleotide. Generally, differences are limited so that the polynucleotide sequences of the reference and the variant are closely similar overall and, in many regions, identical.

Changes in the polynucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the polynucleotide sequence of the variant may alter the amino acid sequence of a polypeptide encoded by the reference polynucleotide. Such polynucleotide changes may result in amino acid substitutions, additions, deletions, fusions and truncations in tile polypeptide encoded by the reference sequence, as discussed below.

A variant of a polypeptide is a polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. Recombinant variants encoding these same or similar polypeptides may be synthesized or selected by making use of the "redundancy" In the genetic code. Various codon substitutions, such as the silent changes that produce various restriction sites, may be introduced to optimize cloning into a plasmid or viral vector or expression in a particular prokaryotic or eukaryotic system. Mutations may also be introduced to modify the properties of the polypeptide, to change ligand-binding affinities, interchain affinities, or polypeptide degradation or turnover rate.

As discussed herein, minor variations in the amino acid sequences of polypeptides, antibodies or immunoglobulin molecules are contemplated as being encompassed by the present invention, providing that the variations in the amino acid sequence maintain at least 80%, more preferably at least 85%, 90% 95%, and most preferably 99% of the original sequence. In particular, conservative amino acid replacements are contemplated. Conservative replacements are those that take place within a family of amino acids that are related in their side chains. Genetically encoded amino acids are generally divided into families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cysteine, serine, threonine, tyrosine). More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by comparing the specific activity of the polypeptide derivative with the unmodified polypeptide. For purposes of this application, the invention encompasses variants of the claimed antibodies which maintain a binding affinity ($K_D$) less than 1 μM for an RG1 epitope.

The following terms are used to describe the sequence relationships between two or more polynucleotide or amino acid sequences: "reference sequence", "comparison window", "sequence identity", "percentage of sequence identity", "substantial identity", "similarity", and "homologous". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24. nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence. The term "similarity", when used to describe a polypeptide, is determined by comparing the amino acid sequence and the conserved amino acid substitutes of one polypeptide to the sequence of a second polypeptide. The term "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides.

"Antibody" or "antigen-binding antibody fragment" refers to an intact antibody, or a fragment thereof, that competes with the intact antibody for specific binding. An antibody or antigen-binding antibody fragment, is said to specifically bind an antigen when the dissociation constant is less than or equal to 1 μM, preferably less than or equal to 100 nM and most preferably less than or equal to 10 nM. Binding can be measured by methods known to those skilled in the art, an example being the use of a BIAcore™ instrument. Antibody fragments comprise a portion of an intact antibody, preferably the antigen binding or variable region of the intact antibody. Binding fragments include Fab, Fab', F(ab')$_2$, and Fv fragments; diabodies; linear antibodies; single-chain antibody molecules; and multispecific antibodies formed from antibody fragments (C. A. K Borrebaeck, editor (1995) *Antibody Engineering* (*Breakthroughs in Molecular Biology*), Oxford University Press; R. Kontermann & S. Duebel, editors (2001) *Antibody Engineering* (Springer Laboratory Manual), Springer Verlag). An antibody other than a "bispecific" or "bifunctional" antibody is understood to have each of its binding sites identical.

"Epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. Two antibodies are said to "bind the same epitope" if one antibody is shown to compete with the second antibody in a competitive binding assay, by any of the methods well known to those of skill in the art.

"Recombinant" or "recombinant DNA molecule" refers to a polynucleotide sequence which is not naturally occurring, or is made by the artificial combination of two otherwise separated segments of sequence. By "recombinantly produced" is meant artificial combination often accomplished by either chemical synthesis means, or by the artificial manipulation of isolated segments of polynucleotides, e.g., by genetic engineering techniques. Such manipulation is usually done to replace a codon with a redundant codon encoding the same or a conservative amino acid, while typically introducing or removing a sequence recognition site. Alternatively, it is performed to join together polynucleotide segments with desired functions to generate a single genetic entity comprising a desired combination of functions not found in the common natural forms. Restriction enzyme recognition sites, regulation sequences, control sequences, or other useful features may be incorporated by design. "Recombinant DNA molecules" include cloning and expression vectors. "Recombinant" may also refer to a polynucleotide which encodes a polypeptide and is prepared using recombinant DNA techniques.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. For example, with respect to polynucleotides, the term isolated means that it is separated from the chromosome and cell in which it naturally occurs. Polynucleotides and polypeptides may occur in a composition, such as media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

"Substantially pure" and "substantially homogenous" are used interchangeably and describe RG1 polypeptide, or fragments thereof, or a polynucleotide segment encoding same, where such polypeptide or polynucleotide is separated from components that naturally accompany it. An RG1 polypeptide or fragment thereof, or DNA segment encoding same is substantially free of naturally-associated components when it is separated from the native contaminants which accompany it in its natural state. Thus, a polypeptide that is chemically synthesized or synthesized in a cellular system different from the cell in which it naturally originates will be substantially free from its naturally-associated components. Similarly, a polynucleotide that is chemically synthesized or synthesized in a cellular system different from the cell in which it naturally originated will be substantially free from its naturally-associated components.

"Polymerase chain reaction" or "PCR" refers to a procedure wherein specific pieces of DNA are amplified as described in U.S. Pat. No. 4,683,195, issued 28 Jul. 1987. Generally, sequence information from the ends of the polypeptide fragment of interest or beyond needs to be available, such that oligonucleotide primers can be designed; these primers will point towards one another, and will be identical or similar in sequence to opposite strands of the template to be amplified. The 5' terminal nucleotides of the two primers will coincide with the ends of the amplified material. PCR can be used to amplify specific DNA sequences from total genomic DNA, cDNA transcribed from total cellular RNA, plasmid sequences, etc. (See generally Mullis et al., *Cold Spring Harbor Symp. Quant Biol.*, 51: 263, 1987; Erlich, ed., PCR Technology, Stockton Press, NY, 1989).

"Stringency" typically occurs in a range from about $T_m$, (melting temperature)-5° C. (5° below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. As herein used, the term "stringent conditions" means hybridization will occur only if there is at least 95% and preferably at least 97% identity between the sequences.

"Hybridization" as used herein, shall include "any process by which a polynucleotide strand joins with a complementary strand through base pairing" (Coombs, J., Dictionary of Biotechnology, Stockton Press, New York, N.Y., 1994).

"Therapeutically effective dose" refers to that amount of polypeptide or its antibodies, antagonists, or inhibitors, including antisense molecules and ribozymes, which ameliorate the symptoms or conditions of a disease state. A dose is considered a therapeutically effective dose in the treatment of cancer or its metastasis when tumor or metastatic growth is slowed or stopped, or the tumor or metastasis is found to shrink in size, so as to lead to an extension in life span for the subject. A dose is also considered therapeutically effective if it leads to an improvement in the overall quality of life of the patient, i.e. alleviation of pain. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$.

"Treating" or "treatment" as used herein covers the treatment of a disease-state in a human patient, which disease-state includes disease states which are characterized by an increased level of RG1, such as prostate cancer or advanced metastatic prostate cancer.

DETAILED DESCRIPTION OF THE INVENTION

Antibodies

The present invention relates to antibodies, antigen-binding antibody fragments thereof, and variants of the antibodies and fragments, that specifically bind to an RGI polypeptide, particularly to the RG1 polypeptide having the amino acid sequence of SEQ ID NO: 2. These antibodies can be, for example, polyclonal or monoclonal antibodies. More preferred are monoclonal antibodies. Still more preferred are chimeric or humanized antibodies, and still more preferred are human antibodies.

The antibodies, antigen-binding antibody fragments, and variants of the antibodies and fragments, contemplated in the present invention bind to an epitope of the RGI polypeptide with a dissociation constant ($K_D$) less than or equal to 1 µM. More preferred are antibodies which bind with a $K_D$ less than or equal to 100 nM. Most preferred are antibodies which bind with a $K_D$ less than or equal to 10 nM. Also contemplated are antibodies which recognize and bind to the same epitope as the epitope bound by the antibodies described below, and which can be determined through competitive binding studies, using techniques well-known to those skilled in the art.

The antibodies, antigen-binding antibody fragments, and variants of the antibodies and fragments of the invention are comprised of a light chain variable region and a heavy chain variable region. Among the preferred embodiments of the invention in this regard are antibodies, antigen-binding antibody fragments thereof, or variants thereof, comprising a light chain variable region having at least 80%, more preferrably at least 90%, still more preferrably at least 95%, and still more preferrably 99% sequence identity to the amino acid sequences of SEQ ID NO: 26 or SEQ ID NO: 29. Also preferred embodiments are antibodies, antigen-binding antibody fragments thereof, or variants thereof, comprising a heavy chain variable region having at least 80%, more preferrably at least 90%, still more preferrably at least 95%, and still more preferrably 99% sequence identity to the amino acid sequences of SEQ ID NO: 27, SEQ ID NO: 28, SEQ ID NO: 30 or SEQ ID NO: 31 (see FIGS. 3 and 4).

Particularly preferred embodiments of the invention are antibodies or antigen-binding antibody fragments thereof, or variants thereof, comprising a light chain variable region having the amino acid sequence SEQ ID NO: 26 or SEQ ID NO: 29, which are encoded by the nucleotide sequences SEQ ID NOS: 20 and 23, respectively.

Also particularly preferred are antibodies, or antigen-binding antibody fragments thereof, or variants thereof, comprising a heavy chain variable region having an amino acid sequence chosen from SEQ ID NOS: 27, 28, 30 or 31, which are encoded by the nucleotide sequences SEQ ID NOS. 21, 22, 24 and 25, respectively.

More particularly preferred in this regard are an antibody, or antigen-binding antibody fragment thereof, or a variant thereof, comprising a light chain variable region having the amino acid sequence SEQ ID NO: 26 and further comprising a heavy chain variable region having the amino acid sequence SEQ ID NO:27 or SEQ ID NO: 28 and a second antibody comprising a light chain variable region having the amino acid sequence SEQ ID NO: 29 and further comprising a heavy chain variable region having the amino acid sequence SEQ ID NO: 30 or SEQ ID NO: 31.

Most preferred are the human antibodies, or antigen-binding antibody fragments thereof, or variants thereof, as follows: (a) an antibody comprised of a light chain variable region having the amino acid sequence SEQ ID NO: 26 and a heavy chain variable region having the amino acid sequence SEQ ID NO: 27, (b) an antibody comprised of a light chain variable region having the amino acid sequence SEQ ID NO: 26 and a heavy chain variable region having the amino acid sequence or SEQ ID NO: 28, (c) an antibody comprised of a light chain variable region having the amino acid sequence SEQ ID NO: 29 and a heavy chain variable region having the amino acid sequence SEQ ID NO: 30, or (d) an antibody comprised of a light chain variable region having the amino acid sequence SEQ ID NO: 29 and a heavy chain variable region having the amino acid sequence or SEQ ID NO: 31.

Antibody Production

RG1 polypeptides, fragments or derivatives, or cells expressing them can be used as an immunogen to produce antibodies thereto (Harlow, Antibodies, Cold Spring Harbor Press, NY (1989)). Various procedures known in the art may be used for the production of such antibodies and fragments (C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag).

Antibodies generated against RG1 can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide. Alternate methods that do not require the use of purified RG1 protein or RG1 peptides to generate antibodies to RG1, include 'DNA immunization' in which an expression vector or virus is created using DNA coding for RG1 and is used to transfect or infect host tissue cells to express RG1 in the animal used to generate antibodies, or cell based immunization in which cell lines expressing RG1 created in vitro are used in the immunization procedure.

Monoclonal antibodies can be prepared using any technique which provides antibodies produced by continuous cell line cultures. Examples include the hybridoma technique (Kohler and Milstein, *Nature* 256: 495-497, 1975), the human B-cell hybridoma technique (Kozbor et al., Immunology Today 4: 72, 1983) and the EBV-hybridoma technique to produce human monoclonal antibodies (Cole et al., in *Monoclonal Antibodies and Cancer*, Alan R. Liss, Inc., 77-96, 1985). For cell based immunizations using cell lines expressing RG1, subtractive immunization may be used to immunotolerize the animals to the parent cell line (Sleister, H. M. and Rao, A. G., *J. Immunological Methods* 261:213-220, 2002).

In addition, techniques developed for the production of "chimeric antibodies", the splicing of mouse antibody genes to human antibody genes to obtain a molecule with appropriate antigen specificity and biological activity can be used (Morrison et al., *Proc. Natl. Acad. Sci. USA* 81:6851-6855, 1984; Neuberger et al., *Nature* 312:604-608, 1984; Takeda et al., *Nature* 314:452-454, 1985). Alternatively, techniques described for the production of single chain antibodies (U.S. Pat. No. 4,946,778) can be adapted to produce RG1-specific single chain antibodies.

Furthermore, "human" antibodies can be produced using the methods described in U.S. Pat. Nos. 5,877,397 and 5,569,825, which are incorporated herein in full by reference, or through use of the XENOMOUSE™, as described in Mendez et al. *Nature Genetics* 15:146-156, 1997. Such antibodies can also be generated using phage display technology (Rader et al., *Current Opinion in Biotechnology* 8:155-I 168, 1997; Aujame et al., *Human Antibodies* 8:155-168, 1997). The generation of human antibodies is very attractive, in that such antibodies are expected to minimize the immunogenic and allergic responses intrinsic to mouse or mouse-derived monoclonal antibodies. Generation of human antibodies which recognize epitopes of the RG1 polypeptide (SEQ ID NO: 2) are described In Example 4.

Antibodies may also be produced by inducing in vivo production in the lymphocyte population or by screening recombinant immunoglobulin libraries or panels of highly specific binding reagents as disclosed in Orlandi et al. (*Proc. Natl. Acad. Sci. USA* 86:3833-3837, 1989) and Winter and Milstein (*Nature* 349:293-299, 1991).

Antibody fragments which contain specific binding sites for RG1 may also be generated. There are often advantages to using antibody fragments, rather than whole antibodies, since the smaller size of the fragments can lead to more rapid clearance, and may also provide improved access to solid tumors.

Such fragments include, but are not limited to the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., *Science* 256:1270-1281, 1989). Fab, Fv and ScFv antibody fragments can all be expressed in and secreted from *E. coli*, or a variety of eukaryote cell expression systems, allowing for the production of large amounts of these fragments. Alternatively, Fab'-SH fragments can be directly recovered from *E. coli* and chemically coupled to form F(ab')$_2$ fragments (Carter et al., Bio/Technology 10:163-167 (1992)). Other techniques for the production of antibody fragments are known to those skilled in the art. Single chain Fv fragments (scFv), diabodies, minibodies and other engineered antibody fragments are also envisioned (see U.S. Pat. No. 5,576,184 and U.S. Pat. No. 5,587,458; Hudson et al. *Nature Medicine* 9:129-133, 2003)). Fv and sFv fragments are examples of species with intact combining sites that are devoid of constant regions; thus, they are likely to show reduced nonspecific binding during in vivo use, and are particularly preferred for use as imaging agents (C. A. K Borrebaeck, editor (1995) *Antibody Engineering* (*Breakthroughs in Molecular Biology*), Oxford University Press; R. Kontermann & S. Duebel, editors (2001) *Antibody Engineering* (Springer Laboratory Manual), Springer Verlag). The antibody fragment may also be a "linear antibody" e.g., as described in U.S. Pat. No. 5,641,870, for example. Such linear antibody fragments may be monospecific or bispecific.

Variants of the antibodies or antibody fragments described herein are also contemplated, and can be made using any of the techniques and guidelines for conservative and non-conservative mutations, e.g., U.S. Pat. No. 5,364,934. Variations include substitution, deletion or insertion of one or more codons encoding the antibody, resulting in a change in the amino acid sequence as compared with the native antibody sequence. The utility of such variations contemplated would include those leading to (1) a reduction in susceptibility to proteolysis or inactivation by oxidation, (2) an alteration in binding affinity for forming protein complexes or binding affinities to antigens, (3) an alteration in in vivo clearance or biodistribution, (4) changes in the antibody isotype or allotype, (5) changes in the functional properties of the antibody, for example Fc receptor binding, (6) an alteration in the epitope sequences to decrease or increase immunogenicity, and (7) other changes in physicochemical or functional properties of such analogs. Guidance in determining which amino acid residue my be inserted, substituted or deleted without adversely affecting the desired activity may be found by minimizing the number of amino acid sequence changes made in regions of high homology between the RG1 antibodies and that of homologous proteins. The variation allowed may be determined by systematically making insertions, deletions or substitutions of amino acids in the sequence and testing the resulting variants for activity exhibited by the native sequence.

A particularly preferred type of substitutional variant involves substituting one more hypervariable region residues of a parent antibody (e.g. human antibody). Generally, the resulting variant(s) selected for further development will have improved biological properties relative to the parent antibody from which they are generated. A convenient way for generating such substitutional variants involves affinity maturation using phage display (Schier R., *J. Mol. Biol.*, 263:551-67, 1996). The variants are then screened for their biological activity (e.g. binding affinity) as described herein (see Example 4). In order to identify hypervariable region residues which would be good candidates for modification, alanine scanning mutagenesis can be performed to identify hypervariable region residues contributing significantly to antigen binding. Antibodies with superior properties in one or more relevant assays can undergo further development.

The amino acid sequence of RG1 (SEQ ID NO: 2) presented herein may be used to select specific regions of the RG1 polypeptide for generating antibodies. As will be understood by those skilled in the art, the regions or epitopes of an RG1 polypeptide to which an antibody is directed may vary with the intended application. For example, antibodies intended for use in an immunoassay for the detection of membrane-bound RG1 on prostate cells should be directed toward accessible epitopes on the RG1 polypeptide. Regions of the RG1 polypeptide that show immunogenic structure, as well as other regions and domains, can readily be identified using various other methods known in the art, such as Chou-Fasman, Garnier-Robson, or Jameson-Wolf analysis. Fragments containing these residues are particularly suited in generating anti-RG1 antibodies. Useful fragments include, but are not limited to, the sequences PLGGESICSAGAPA-KYSIT (SEQ ID NO: 8); HSSDYSMWRKNQYVS (SEQ ID NO: 10); DAGTDSGFTFSSPNFATIPQDTV (SEQ ID NO: 11); and NEIVDSASVPET (SEQ ID NO: 12). Generation of polyclonal antibodies to these regions is described in Example 4.

Uses of Antibodies Recognizing Epitopes of RG1

The antibodies, antigen-binding antibody fragments, and variants thereof of the invention may be particularly useful in diagnostic assays, imaging methodologies, and therapeutic methods for the management of cancers in which RG1 is overexpressed, including cancers of the prostate, kidney, colon, and ovaries.

The invention provides various immunological assays useful for the detection of RG1 polypeptides and for the diagnosis of cancers, such as prostate cancer. Such assays generally comprise one or more RG1 antibodies capable of recognizing and binding a RG1 polypeptide. The most preferred antibodies will selectively bind to RG1 and will not bind (or bind weakly) to non-RG1 polypeptides. The assays include various immunological assay formats well known in the art, including but not limited to various types of radioimmunoassays, enzyme-linked immunoabsorbent assays, and the like. In addition, immunological imaging methods capable of detecting prostate cancer are also provided by the invention, including but not limited to radioscintigraphic imaging methods using labeled RG1 antibodies. Such assays may be clinically useful in the detection, monitoring and prognosis of cancers, such as prostate cancer.

The above-described antibodies may be employed to isolate or to identify clones expressing the polypeptide or to purify the polypeptide of the present invention by attachment of the antibody to a solid support for isolation and/or purification by affinity chromatography.

Additionally, RG1 antibodies may be used to isolate RG1 positive cells using cell sorting and purification techniques. In particular, RG1 antibodies may be used to isolate prostate cancer cells from xenograft tumor tissue, from cells in culture, etc. using antibody-based cell sorting or affinity purification techniques. Other uses of the RG1 antibodies of the invention include generating anti-idiotypic antibodies that mimic the RG1 polypeptide.

RG1 antibodies can be used for detecting the presence of prostate cancer or tumor metastasis. The presence of such RG1-containing cells within various biological samples, including serum, prostate and other tissue biopsy specimens, may be detected with RG1 antibodies. In addition, RG1 antibodies may be used in various imaging methodologies such as immunoscintigraphy with a $^{99m}$Tc (or other isotope) conjugated antibody. For example, an imaging protocol similar to the one recently described using an $^{111}$In conjugated anti-PSMA antibody may be used to detect recurrent and metastatic prostate carcinomas (Sodee et al., Clin. Nuc. Med. 21: 759-766, 1997). Another method of detection that can be used is positron emitting tomography (see Herzog et al., J. Nucl. Med. 34:2222-2226, 1993).

The RG1 antibodies of the invention may be labeled with a detectable marker or conjugated to a second molecule, such as a cytotoxic agent, and used for targeting the second molecule to a RG1 positive cell (Vitetta, E. S. et al., Immunotoxin Therapy, in DeVita, Jr, V. T. et al., eds, Cancer: Principles and Practice of Oncology, 4$^{th}$ ed., J. B. Lippincott Co., Philadelphia, 2624-2636, 1993). Examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, diptheria toxin, epothilones, Pseudomonas exotoxin (PE) A, PE40, abrin, and glucocorticoid and other chemotherapeutic agents, as well as radioisotopes. Cytotoxic or antiproliferative targeted fusion proteins may be created by genetic or chemical fusion of the antibody to an appropriate cytokine, chemokine, interferon, or growth factor that has the desired anti-tumor biological activity (Asgeirsdottir et al., Biochem. Pharmacol. 15:1729-1739, 2003). Suitable detectable markers include, but are not limited to, a radioisotope, a fluorescent compound, a bioluminescent compound, chemiluminescent compound, a metal chelator or an enzyme. Suitable radioisotopes for immunotherapy or for use as a detectable marker include the following: Antimony-124, Antimony-125, Arsenic-74, Barium-103, Barium-140, Beryllium-7, Bismuth-j206, Bismuth-207, Cadmium-109, Cadmium-115m, Calcium-45, Cerium-139, Cerium-141, Cerium-144, Cesium-137, Chromium-51, Cobalt-56, Cobalt-57, Cobalt-58, Cobalt-60, Cobalt-64, Erbium-169, Europium-152, Gadolinium-153, Gold-195, Gold-199, Hafnium-175, Hafnium-181, Indium-111, Iodine-123, Iodine-131, Iridium-192, Iron-55, Iron-59, Krypton-85, Lead-210, Lutetium-177, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-2226, Rhenium-186, Rubidium-86, Ruthenium-103, Ruthenium-106, Scandium-44, Scandium-46, Selenium-75, Silver-110m, Silver-11, Sodium-22, Strontium-85, Strontium-89, Strontium-90, Sulfur-35, Tantalum-182, Technetium-99m, Tellurium-125, Tellurium-132, Thallium-170, Thallium-204, Thorium-228, Thorium-232, Tin-113, Titanium-44, Tungsten-185, Vanadium-48, Vanadium-49, Ytterbium-169, Yttrium-88, Yttrium-90, Zinc-65, and Zirconium-95.

Radiolabeling of antibodies is accomplished using a chelating agent which is covalently attached to the antibody, with the radionuclide inserted into the chelating agent. Preferred chelating agents are set forth in Srivagtava et al. Nucl. Med. Bio. 18:589-603, 1991 and McMurry et al., J. Med. Chem. 41:3546-3549, 1998. or derived from the so-called NOTA chelate published in H. Chong, K. et al., J. Med. Chem. 45:3458-3464, 2002, all of which are incorporated herein in full by reference. Particularly preferred for conjugation of radioisotopes to an RG1 antibody are derivatives of the bifunctional chelator p-SCN-Benzyl-DTPA (Brechbiel et al. Inorg. Chem. 25:2772-2781, 1986); for example, cyclohexyl-DTPA (CHX-A"-DTPA, Wu et al., Bioorg. Med. Chem. 10:1925-1934. 1997) and MX-DTPA (1B4M-DTPA, McMurry et al., J. Med. Chem., 41: 3546-3549, 1996), as well as 1,4,7-triazacyclononane-N,N',N"-triacetic acid (NOTA) (Chong et al. J. Med. Chem. 45:3458-3464, 2002). Conjugation can be accomplished by the method of Nikula et al. Nucl. Med. Biol. 3:387-390, 1995. Particularly preferred for use as a detectable marker for immunoscintigraphy are the radioisotopes $^{111}$In or $^{99m}$Tc. Preferred detectable markers for positron emitting tomography are $^{43}$Sc, $^{44}$Sc, $^{52}$Fe, $^{55}$Co, $^{68}$Ga, $^{64}$Cu, $^{186}$Y and $^{94m}$Tc. For immunotherapy, the beta-emitting radioisotopes $^{46}$Sc, $^{47}$Sc, $^{48}$Sc, $^{72}$Ga, $^{73}$Ga, $^{90}$Y, $^{67}$Cu, $^{109}$Pd, $^{111}$Ag, $^{149}$Pm, $^{153}$Sm, $^{166}$Ho, $^{177}$Lu, $^{186}$Re, and $^{188}$Re and the alpha-emitting isotopes $^{211}$At, $^{211}$Bi, $^{212}$Bi, $^{213}$Bi and $^{214}$Bi, can be used. Preferred are $^{90}$Y, $^{177}$Lu, $^{72}$Ga, $^{153}$Sm, $^{67}$Cu and $^{212}$Bi, and particularly preferred are $^{90}$Y and $^{177}$Lu.

Immunotherapy for Prostate and Other Cancers

The invention provides various immunotherapeutic methods for treating prostate and other cancers, including antibody therapy, in vivo vaccines, and ex vivo immunotherapy approaches. Other cancers include cancer of the kidney, colon, and ovaries. In one approach, the invention provides RG1 antibodies which may be used systemically to treat prostate cancer. For example, unconjugated RG1 antibodies may be introduced into a patient such that the antibody binds to RG1 on, in or associated with prostate cancer cells and mediates the destruction of the cells, and the tumor, by mechanisms which may include complement-mediated cytolysis, antibody-dependent cellular cytotoxicity, altering the physiologic function of RG1, and/or the inhibition of ligand binding or signal transduction pathways. RG1 antibodies conjugated to toxic agents such as ricin or radioisotopes, as described above, may also be used therapeutically to deliver the toxic agent directly to RG1-bearing prostate tumor cells and thereby destroy the tumor cells.

Prostate cancer immunotherapy using RG1 antibodies may follow the teachings generated from various approaches which have been successfully employed with respect to other types of cancer, including but not limited to colon cancer (Arlen et al., *Crit. Rev. Immunol.* 18: 133-138, 1998), multiple myeloma (Ozaki et al., *Blood* 90: 3179-3186, 1997; Tsunenari et al., *Blood* 90: 2437-2444, 1997), gastric cancer (Kasprzyk et al, *Cancer Res.* 52: 2771-2776, 1992), B-cell lymphoma (Funakoshi et al., *Immunther. Emphasis Tumor Immunol.* 19: 93-101, 1996), leukemia (Zhong et al., *Leuk. Res.* 20: 581-589, 1996), colorectal cancer (Moun et al., *Cancer Res.* 54: 6160-6166, 1994; Velders et al., *Cancer Res.* 55:4398-4403, 1995), and breast cancer (Shepard et al., *J. Clin. Immunol.* 11: 117-127, 1991).

The invention further provides vaccines formulated to contain an RG1 polypeptide or fragment thereof. The use of a tumor antigen in a vaccine for generating humoral and cell-mediated immunity for use in anti-cancer therapy is well known in the art and has been employed in prostate cancer using human PSMA and rodent PAP immunogens (Hodge et al., *Int. J. Cancer* 63: 231-237, 1995: Fong et al., *J. Immunol.* 159: 3113-3117, 1997). Such methods can be readily practiced by employing an RG1 polypeptide, or fragment thereof, or an RG1-encoding nucleic acid molecule and recombinant vectors capable of expressing and appropriately presenting the RG1 immunogen.

For example, viral gene delivery systems may be used to deliver a RG1-encoding nucleic acid molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, in *Curr. Opin, Immunol.* 8: 658-663, 1996). Non-viral delivery systems may also be employed by using naked DNA encoding a RG1 polypeptide or fragment thereof introduced into the patient (i.e., intramuscularly) to induce an anti-tumor response. In one embodiment, the full-length human rg1 cDNA may be employed. In another embodiment, human rg1 cDNA fragments may be employed. In another embodiment, rg1 nucleic acid molecules encoding specific T lymphocyte (CTL) epitopes may be employed. CTL epitopes can be determined using specific algorithims (e.g., Epimer, Brown University) to identify peptides within a RG1 polypeptide which are capable of optimally binding to specified HLA alleles.

Various ex vivo strategies may also be employed. One approach involves the use of dendritic cells to present a RG1 polypeptide as antigen to a patient's immune system. Dendritic cells express MHC class I and II, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., *Prostate* 28: 65-69, 1996; Murphy et al., *Prostate* 29: 371-380, 1996). Dendritic cells can be used to present RG1 polypeptides to T cells in the context of MHC class I and II molecules. In one embodiment, autologous dendritic cells are pulsed with RG1 polypeptides capable of binding to MHC molecules. In another embodiment, dendritic cells are pulsed with the complete RG1 polypeptide. Yet another embodiment involves engineering the overexpression of the rg1 gene in dendritic cells using various implementing vectors known in the art, such as adenovirus (Arthur et al., *Cancer Gene Ther.* 4: 17-25, 1997), retrovirus (Henderson et al., *Cancer Res.* 56: 3763-3770, 1996), lentivirus, adeno-associated virus. DNA transfection (Ribas et al., *Cancer Res.* 57: 2865-2869, 1997), and tumor-derived RNA transfection (Ashley et al., *J. Exp. Med.* 186: 1177-1162, 1997).

Anti-idiotypic anti-RG1 antibodies can also be used in anti-cancer therapy as a vaccine for inducing an immune response to cells expressing an RG1 polypeptide. Specifically, the generation of anti-idiotypic antibodies is well known in the art and can be readily adapted to generate anti-idiotypic anti-RG1 antibodies that mimic an epitope on a RG1 polypeptide (see, for example, Wagner et al., *Hybridoma* 16: 33-40, 1997: Foon et al., *J. Clin. Invest* 96: 334-342, 1995; Herlyn et al., *Cancer Immunol Immunother* 43: 65-76, 1996). Such an anti-idiotypic antibody can be used in anti-idiotypic therapy as presently practiced with other anti-idiotypic antibodies directed against tumor antigens.

Genetic immunization methods may be employed to generate prophylactic or therapeutic humoral and cellular immune responses directed against cancer cells expressing RG1. Using the RG1-encoding DNA molecules described herein, constructs comprising DNA encoding an RG1 polypeptide/immunogen and appropriate regulatory sequences may be injected directly into muscle or skin of an individual, such that the cells of the muscle or skin take up the construct and express the encoded RG1 polypeptide/immunogen. The RG1 polypeptide/immunogen may be expressed as a cell surface polypeptide or be secreted. Expression of the RG1 polypeptide/immunogen results in the generation of prophylactic or therapeutic humoral and cellular immunity against prostate cancer. Various prophylactic and therapeutic genetic immunization techniques known in the art may be used. (for a review, see information and references published at internet address worldwideweb.genweb.com).

Assays for Identifying Agents Binding to RG1

The present invention also relates to assays and methods which can be used to identify agents (i.e. an antibody, peptide, etc.) that bind to RG1. Specifically, agents that bind to RG1 can be identified by the ability of the RG1 ligand or other agent or constituent to bind to RG1 and/or the ability to inhibit/stimulate RG1 activity.

As described above, antibodies are obtained by immunization of suitable mammalian subjects with peptides, containing as antigenic regions, those portions of the RG1 polypeptide intended to be targeted by the antibodies. Such agents can be used in competitive binding studies to identify second I generation inhibitory agents as well as to block RG1 activity.

Agents that bind a RG1 polypeptide, such as a RG1 antibody, can be used to modulate the 5 activity of RG1, to target anticancer agents to appropriate mammalian cells, or to identify agents that block the interaction with RG1. Cells expressing RG1 can be targeted or identified by using an agent that binds to RG1.

How the RG1 binding agents will be used depends on the nature of the RG1 binding agent. For example, a RG1 binding agent can be used to: deliver conjugated toxins, such as diphtheria toxin, cholera toxin, ricin or pseudomonas exotoxin, to a RG1 expressing cell; modulate RG1 activity; to directly kill a RG1 expressing cell; or in screens to identify competitive binding agents. For example, a RG1 inhibitory agent can be used to directly inhibit the growth of RG1 expressing cells whereas a RG1 binding agent can be used as a diagnostic agent.

Pharmaceutical Compositions and Administration

The present invention also relates to pharmaceutical compositions which may comprise rg1 polynucleotides, RG1 polypeptides, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

The present invention also relates to the administration of pharmaceutical compositions. Such administration is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxilliaries which facilitate processing of the active compounds into preparations which can be used pharmaceutically. Further details on techniques for formulation and administration may be found in the latest edition of *Remington's Pharmaceutical Sciences* (Ed. Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxilliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl, cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol and/or titanium dioxide, lacquer solutions, and suitable organic solvents or solvent mixtures. Dyestuffs or pigments may be added to the tablets or dragee coatings for product identification or to characterize the quantity of active compound, i.e. dosage.

Pharmaceutical preparations that can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture use or sale of pharmaceuticals or biological products, reflecting approval by the agency of the manufacture, use or sale of the product for human administration.

Manufacture and Storage.

The pharmaceutical compositions of the present invention may be manufactured in a manner that is known in the art, e.g., by means of conventional mixing, dissolving, granulating, dragee-making, levigating, emulsifying, encapsulating, entrapping or lyophilizing processes.

The pharmaceutical composition may be provided as a salt and can be formed with may acids, including by not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of RG1, such labeling would include amount, frequency and method of administration.

Therapeutically Effective Dose.

Pharmaceutical compositions suitable for use in the present invention include compositions wherein the active ingredients are contained in an effective amount to achieve the intended purpose, i.e. treatment of a particular disease state characterized by RG1 expression. The determination of an effective dose is well within the capability of those skilled in the art.

For any compound, the therapeutically effective dose can be estimated initially either in cell culture assays, e.g., neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors that ameliorate the symptoms or condition. Therapeutic efficacy and toxicity of such compounds can be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies is used in formulating a range of dosage for human use. The dosage of such compounds lies preferably within a range of circulating concentrations what include the $ED_{50}$, with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for polynucleotides than for proteins or their inhibitors. Similarly, delivery of polynucleotides or polypeptides will be specific to particular cells, conditions, locations, etc. Preferred specific activities for a radiolabeled antibody may range from 0.1 to 10 mCi/mg of protein (Riva et al., *Clin. Cancer Res.* 5:3275s-3280s, 1999; Wong et al., *Clin. Cancer Res.* 6:3855-3863, 2000; Wagner et al., *J. Nuclear Med.* 43:267-272, 2002).

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., *Molecular Cloning: A Laboratory Manual*, 2nd Ed.; Cold Spring Harbor Laboratory Press, Cold Spring Harbor, N.Y., 1989.

Example 1

Identification of Human rg1 Polynucleotide

Rg1 was identified as a gene expressed in the prostate by mining Incyte's LIFESEQ®™database. The nucleotide sequence was identified by an annotation search of the database, using the "Protein Function" tool provided by Incyte for the purpose of searching the database. The nucleotide sequence was found in the category of cell adhesion molecules in the annotated database and was described as a homologue of f-spondin. Electronic Northern analysis of the distribution of rg1 polynucleotide sequences in the set of libraries in the database revealed that rg1 was expressed at high levels in the prostate libraries and at lower levels in a number of other tissue libraries, including those from normal and tumor tissues.

Following assembly of the set of rg1 clones in the database into a contiguous polynucleotide sequence, and editing of the contiguous sequence, a full-length coding sequence was identified in the predicted assembled polynucleotide. This sequence coded for a protein homologous to f-spondin and to Mindin-2.

Incyte clones 1640796, 1712252, and 1880265 were obtained from Incyte for experimental work and clone 3360733 was identified as containing the most 5' nucleotide sequence. This clone was fully sequenced and contained the full coding sequence for the predicted RG1 protein. This sequence is shown in SEQ D NO: 1.

Example 2

Rg1 mRNA Expression

The expression of rg1 mRNA in a variety of samples from normal and tumor tissues and in cell lines, was determined by semi-quantitative PCR using a Taqman assay, (Perkin-Elmer). Prostate normal, benign and tumor tissue samples that had been graded according to a modified Gleason grading system were obtained from the Urology Department at Stanford University School of Medicine. RNA was isolated from these by standard procedures. RNA from other tumor and normal tissues was purchased from commercial sources, including Clonetech, and Biochain. Prostate tumor cell lines, (PC-3, LNCaP and DU145), were obtained from American Type Culture Collection and propagated in culture by standard methods using serum containing medium. Xenograft tumors derived from these cell lines were established in nude mice and harvested from the mice approximately 4-6 weeks after implantation. RNA was isolated from the tumors by standard procedures.

Taqman based PCR analysis was performed using the primers: CGC GCA TAG CTC CGA CTA C (SEQ ID NO: 3)

and GCC GCG TCC GCA AAG (SEQ ID NO: 4) and the Taqman probe: 6-FAM-AGG AAG AAC CAG TAC GTC AGT AAC GGG CTG-Tamra (SEQ ID NO: 5).

These primers and probe were designed using Perkin Elmer's Primer Express software and were synthesized by Synthetic Genetics. PCR reactions were carried out for 30-40 cycles and quantified using prostate RNA to generate a standard curve for relative comparison. This analysis demonstrated that rg1 mRNA was detected at highest abundance in the prostate and at significantly lower levels in several other tissues.

Example 3

Production of RG1 in BHK Cells

Cloning: The RG1 coding region was obtained from Incyte plasmid 3360733. The coding sequence was PCR amplified with primers SST115 (5'-TCCCTCTAGAGCCACCATG-GAAAACCCCAGCCCGGC-3') (SEQ 10 NO: 6) and SST113 (5'-AAGGCATCACGTGTTAGACGCAGTTAT-CAGGGACG-3') (SEQ ID NO: 7) in a standard PCR reaction (100 ul) using 1×Pfu Turbo polymerase buffer (Stratagene, La Jolla, Calif.)/200 uM dNTPs/0.2 uM oligonucleotide primers/2.5 U Pfu Turbo polymerase (Stratagene). PCR amplification conditions were as follows: 3 mins at 95° C., (15 seconds at 95° C., 30 seconds at 60° C., 2 minutes at 72° C.)×35, 72° C. for 7 minutes. The resulting PCR amplified product was purified using a QIAquick PCR column (Qiagen, Valencia, Calif.) and digested with Xbal and Pmll restriction enzymes to result in a 1010 bp fragment that was purified from a 1% agarose gel using a BIO 101 GeneClean Kit (Vista, Calif.). The purified fragment was ligated (using Epicientre Fast Link Kit, (Epicenter, Madison, Wis.) to the noncytopathic Sindbis expression vector pSINrep21 (Agapov et al, 1998, *PNAS* 95: 12989-12994) digested with Xbal and Pmll, and transformed into DH5 alpha competent cells (Life Technologies, Gaithersburg, Calif.) and selected on LB agar plates containing ampicillin (100 ug/ml). One such ampicillin resistant colony was grown in LB medium with ampicillin and shown by sequence analysis to contain the inserted RG1 coding sequence. This plasmid was called pPEG6.

Expression: Two micrograms of pPEG6 was used to transfect 1-3×10$^5$ bovine hamster kidney cells (BHK) cells using Lipofectamine Plus reagent (Life Technologies, Gaithersburg, Md.) according to the manufacturer's instructions. Following transfection, cells were incubated in DMEM plus fetal blood serum for 24-48 hours, at which time the cells were split 1 to 10 and selection for the plasmid containing cells was initiated by adding puromycin (2.5 ug/ml final concentration) arid DMEM containing serum. After the cells were confluent (4-5 days post puromycin addition) the cells were washed with PBS, split 1 to 10, and DMEM medium with serum and 5 ug/ml puromycin was added. After an additional 2-3 days, the medium was replaced with DMEM and 5 ug/ml puromycin without serum, grown for 2-3 days and the presence of RG1 protein was detected in the medium by Western analysis using RG1 antibodies. RG1 protein was detected at a level of 1 ug/ml.

Purification: Baby hamster kidney cells (BHK), transfected to stably overexpress and secrete RG1 protein into the growth medium, were cultured in medium containing fetal bovine serum. When subconfluent, the cells were switched to serum-free medium for 24-48 hours. The medium was collected, centrifuged to remove cells and stored at −80 degrees C. Media was thawed immediately prior to purification and kept on ice. Protease inhibitors were added, media was diluted ten-fold with cold 20 mM Sodium acetate buffer, pH 6.5 and kept at 4 degrees C. throughout the purification. The diluted sample was loaded onto a Q-Sepharose anion exchange column at a flow rate of 0.5 ml/min then washed with the same buffer. Elution was performed using a linear NaCl gradient (0-80% of 1 M NaCl in buffer, 0.5% per minute) while collecting fractions. The RG1 eluted at approximately 75 mM NaCl, as determined by SDS PAGE and Western blot. RG1 containing fractions were pooled, concentrated by ultrafiltration and further purified over a Superdex 75 gel filtration column. Purified BHK-RG1 was used as immunogen in the generation of human mabs that are specific for native RG1 (nRG1) protein, and as antigen in the screening and characterization of these antibodies.

Example 4

Antibody Generation

Polyclonal antibodies: Rabbit polyclonal antisera were raised against five synthetic polypeptide sequences derived from the RG1 protein sequence. These sequences were selected because of their predicted positions at the surface of the protein, in order to generate antisera that are more likely to recognize surface epitopes. Cysteine residues were replaced with aminobutyric acid (Abu) to aid synthesis. The specific amino acid sequences, positions on the RG1 protein and designations for the five peptides are listed below.

| Designation | Position | Amino Acid Sequence | |
|---|---|---|---|
| 1C | 28-46 | PLGGESICSAGAPAKYSIT | (SEQ ID NO: 8) |
| 2C | 46-64 | TFTGKWSQTAFPKQYPLFR | (SEQ ID NO: 9) |
| 3C | 77-91 | HSSDYSMWRKNQYVS | (SEQ ID NO: 10) |
| 4C | 188-210 | DAGTDSGFTFSSPNFATIPQDTV | (SEQ ID NO: 11) |
| 5C | 263-274 | NEIVDSASVPET | (SEQ ID NO: 12) |

Peptides were covalently coupled to keyhole limpet hemocyanin (KLH), via an additional carboxyl-terminal cysteine, for use as an immunogen. Similarly, a bovine serum albumin (BSA) conjugate was prepared for the analysis of antisera titers via ELISA.

Two animals were immunized with each peptide. Initial immunizations were performed in Freunds complete adjuvant (0.5 mg/animal), followed by boosts at three week intervals with 0.25 mg/animal in Freunds incomplete adjuvant applied intramuscularly. Periodic test bleeds were taken and antibody titers against the specific BSA-peptide conjugate were measured by ELISA and compared with preimmune sera. Antisera against peptides 1C and 3C were shown to be active. Antisera against peptide 2C did not recognize RG1 polypeptide. Antisera against peptides 4C and 5C were not tested.

Monoclonal antibodies: Monoclonal antibodies against RG1 were generated by immunizing transgenic mice against RG1 peptides and a 6-histidine-tagged RG1 fusion protein expressed in E. coli. Splenocytes of these animals were fused with myeloma cells to produce hybridoma cells. The resulting hybridomas were screened by ELISA for hybridomas producing antibodies directed against RG1 peptides and protein.

Human monoclonal antibodies with specificity for native RG1 were also prepared by immunization of transgenic mice that contain disrupted mouse heavy and mouse kappa light chain loci. (U.S. Pat. No. 5,877,397). Transgenic mice from C57BL/6J inbred strains (Medarex) were immunized with purified RG1 protein produced in a stable, transfected BHK cell line (see Example 3).

The antigen was mixed with Complete Freunds (Sigma, F5881) adjuvant for the first and second immunization for protocol one; thereafter the antigens were mixed with Incomplete Freunds (Sigma, F5506). For the second protocol Complete Freunds was used for the first immunization and thereafter Incomplete Freunds was used. Each mouse received 25 µg native RG1 (nRG1) in 100 µL PBS, mixed 1:1 with the adjuvant using an emulsifying needle. Mice are injected with 0.2 mL prepared antigen into the peritoneal cavity.

Hybridoma Preparation: The P3 X63 ag8.653 myeloma cell line (ATCC CRL 1580, lot F-15183) was used for the fusions. The original ATCC vial was thawed and expanded in culture. A seed stock of frozen vials was prepared from this expansion. Cells are maintained in culture for 3-6 months, passed twice a week. Supernatant from P388D1 (ATCC, TIB-63 FL) cells was used as conditioned media for the hybridomas. Briefly, cells were grown and expanded to 200 ml. Stationary cultures were grown for ~7 days. The exhausted supernatant was spun down and filtered through a 0.2 pm sterile filter. This cell line is passed for 3-6 months and then a new vial is thawed.

DMEM (Cellgro#10013271, 10013270) containing 5% FBS (Hyclone, #AKE11828), and P/S (Cellgro, #30002029) and were used to culture the myeloma and P388D1 cells. Additional media supplements were added to the Hybridoma growth media, which included 5% Origen—Hybridoma Cloning Factor (IGEN, #36684, 36908), 5% P388D1 conditioned media (Nov. 15, 2000, Dec. 21, 2000 DH), 10% FCS (Hyclone, #AKE11828), β-mercaptoethanol (Gibco #1076640), Genetacin (Gibco #1079874), Hepes (Cellgro-#25060041) and HAT (Sigma, H 0262; $1.0 \times 10^{-4}$ M Hypoxanthine, $4.0 \times 10^{-7}$ M Aminopterin, $1.6 \times 10^{-5}$ M Thymidine), or HT (Sigma, H01 37; $1.0 \times 10^{-4}$ M Hypoxanthine, $1.6 \times 10^{-5}$ M Thymidine).

The splenocytes were fused with myeloma cells using PEG and standard methodology. The resulting hybridomas were plated out into 50 96-well plates, seeded at 200 µl/well for the first fusion. The initial ELISA screen for human IgG,κ antibodies was performed 10-12 days post fusion. Human IgG,κ positive wells were then screened by a 6-His capture ELISA. This screening led to the isolation of 8 human antibodies from 3 fusions: three IgM, one IgG3, and four IgG1 subclass antibodies.

Hybridomas from wells with antigen binding antibodies were first transferred to 24 well plates, and re-screened again for specificity. Native RG1 specific hybridomas were subcloned by limiting dilution to assure monoclonality. Hybridomas producing antibodies that bound native RG1 (nRG1) were preserved at several stages in the development process by freezing cells in IGEN freeze media. Media from these lines was frozen and used for purification of antibodies as described below. Four of the eight were determined to have sufficient specificity to warrant further study.

Purification of antibodies: Four of the human monoclonal antibodies to RG1 described above were purified from cell conditioned media using Protein G Sepharose affinity chromatography. Cells were removed from media by centrifugation and filtration, the media was passed over the Protein G column. The column was then washed in PBS to remove unbound material. Bound antibodies were eluted with 100 mM glycine, pH 2.5 and immediately neutralized by adding 10% v/v 1M Tris, pH 8 to the fractions. Fractions containing antibody were pooled, dialysed into PBS, tested for purity by SDS PAGE, and assayed for antigen binding activity by ELISA.

Screening of Antibodies: Screening of antibodies was performed using several different assay procedures:

A. hIgGγκ ELISA Screen: Ninety-six well microtiter plates (Falcon, #3912) were coated overnight with 1 ug/ml anti-human IgGκ or anti-human IgGκ in PBS (50 ul/well). Plates were aspirated and blocked with PBS 0.05% Tween 20 containing 5% chicken serum for 1 hour at room temperature (1001/well) then washed three times with PBS-tween. Hybridoma supernatants were diluted 1:2 in blocking buffer and incubated for 1 hour at room temperature (100 µl/well) for screening. Following incubation, the plates were washed three times in blocking buffer prior to adding 100 µl/well of secondary antibody (HRP anti-human IgGFc (Jackson, #109-036-098 or HRP anti-human IgGκ (Sigma, #A-7164). The secondary antibody was incubated for 1 hour at room temperature and then the plates were washed 2× in blocking buffer. Plates were developed using 10 ml citrate phosphate buffer, pH 4.0 containing 80 ul ABTS (Sigma, #A1888), 8 µl $H_2O_2$ per plate and read at $A_{415-490}$ nm.

B. RG1 Binding ELISA: Ninety-six well microtiter plates were coated overnight with 0.5-1.0 ug/well purified native RG1 protein in PBS, 50 ul/well, 4 degrees C. The wells were aspirated and then the reaction was blocked with the addition of 100 ul/well PBS-tween+5% chicken serum, followed by incubation for 1 hour at room temperature. Plates were then washed 3 times in blocking buffer. Serially diluted samples (serum, hybridoma supe, purified mabs etc.) were then added to each well, at 50 ul/well. Incubate 1 hour at room temperature then wash 3 times in blocking buffer. The wells are then incubated with HRP anti-human IgGFc secondary antibody in blocking buffer for 1 hour at room temperature and then washed 3 times as before. Plates are developed using substrate described above and measurement of the $A_{405}$ nm using a 96 well plate reader.

C. Capture ELISA Method: In order to determine mab binding to RG1 protein in its native conformation, a capture ELISA format was used. RG1 protein, containing a six histidine expression tag (6His-RGI), was expressed in BHK cells and used as the antigen. The 6His-RG1 was purified from conditioned media using NiNTA agarose affinity chromatography following standard methodology.

Purified 6His RG1 was captured on 96 well NiNTA plates (Qiagen NiNTA H isSorb) using a concentration of 1.5 ug/ml in PBS plus 0.2% BSA (PBS/BSA, 100 ul/well) overnight at 4 degrees C. Wells were washed 3 times with PBS containing 0.05% Tween 20 (PBST). Samples (hybridoma supernatant, sera, purified mabs etc.) were diluted in PBS/BSA and incubated on plates for 1-2 hours at room temperature (50 ul/well) and then washed 3 times with PBST. Secondary antibody (HRP-labeled goat anti-human IgGFc) was diluted 1:5000 in PBS/BSA, added to the plate at 50 ul/well and incubated for 1 hour at room temperature.

Plates were washed 3 times with PBST and developed as in an ELISA. Absorbance at 405 nm was measured using an ELISA plate reader.

D. BIAcore Surface Plasmon Resonance (SPR) Assay: Parental hybridoma supernatants were further screened to qualitatively rank clones by avidity using SPR. A rabbit anti-human IgGFc (Pierce, 31142) was immobilized onto the sensor chip (Biacore, BR-1000-12) using standard amine coupling and 60 ug/ml antibody in acetate pH 4.0 and a mobile phase of HEPES buffered saline (HBS). Hybridoma media was passed over the surface at 5 ul/min to capture onto the surface and then washed to baseline with HBS. Purified, native, BHK-RG1 protein (400 nM) was then passed over the surface and binding was measured by SPR. At the end of the injection, HBS was passed over the surface to measure dissociation of the antibody:RG1 complex. The slope of the SPR measurement over time is indicative of the dissociation rate, the greater the slope, the faster the off rate and therefore the lower avidity of the antibody.

Example 5

Western Blot Analysis of Antibodies

Antisera were tested for RG1 specificity via Western blotting. RG1 specific antisera (those raised against sequences 1C and 3C, above) were tested on RG1 transiently expressed in COS cells, native RG1 secreted from LNCaP cells and RG1 produced from transfected baby hamster kidney cells (BHK). RG1-specific antisera were further tested on lysates prepared from: LNCaP tumors, LNCaP cells, PC3 tumors, PC3 cells and several clinical samples of human prostate tumors. Cells and tissues were lysed in detergent buffer. After boiling for 5 min, 10 ul of each lysate was loaded onto a 12% SDS-polyacrylamide gel to resolve proteins. Separated proteins were then transferred to nitrocellulose membranes. Binding specificity of RG1 antibodies was verified by binding in the presence of the homologous and heterologous peptides. RG1-specific antisera could detect the protein in all samples but PC-3 cells and PC-3 tumors.

Western blot analysis of human mabs specific for native RG1 demonstrated that these antibodies recognized RG1 on blots only under non-reducing conditions. This suggested that these mabs bind to a more native form of RG1.

Example 6

Purification of Native RG1 Protein Secreted from LNCaP Cells

LNCaP cells grown in culture were shown to secrete native RG1 protein by Western blot analysis. In order to purify the native protein, cells were grown for 48 hours in media lacking serum. This serum-free conditioned media was harvested, centrifuged to remove any cells, and concentrated approximately fifty-fold by ultrafiltration. The concentrated media was then diluted ten-fold with 20 mM sodium acetate buffer, pH 6.5 and loaded onto a Q-Sepharose anion exchange column. Column elution consisted of a sodium chloride gradient (0.5% per minute) while collecting 2.0 ml fractions. The RG1 protein eluted at approximately 75 mM NaCl as determined by Western blot and SDS PAGE. The native RG1 protein runs at a slightly lower molecular weight than the 6 histidine-RG1 fusion protein expressed in bacteria, presumably because it lacks the fusion peptide.

Example 7

Immunohistochemical Staining of RG1 Expression in Prostate and Prostate Cancer Metastasis The expression of RG1 protein was determined by LifeSpan Biosciences, Inc. in a variety of human tissues, including kidney, lung, pancreas, muscle, brain and prostate, as well as lymph node and bonemetastasis. Additional prostate tissues were obtained from the Urology Department at Stanford University School of Stanford and tested at Berlex. The tissue sections were deparaffinized using standard procedures. The polyclonal antibody RG1-3C was used as a primary antibody and the detection system consisted of using Vector ABC-AP kit (AK5002) with a Vector red substrate kit (Sk5002). As a negative control, the staining was carried out in the absence of the primary antibody.

Expression of RG1 was examined in prostate tumor and normal prostate tissue from several patients. In all cases, strong staining, representing RG-1 expression, was seen in the prostate tumor samples. RG-1 expression varied in the normal prostate tissue, from almost none to significant staining.

Expression of RG1 was also detected by immunohistochemistry in lymph node and bone samples known to contain prostate tumor metastasis. Normal lymph node or bone do not show staining.

Example 8

Sequencing of RG1 Antibodies

The nucleic acid sequences of two human RG1 antibodies (C and B) generated and purified as described above in Example 4 were determined by standard methods. The nucleotide sequence of the B light chain variable region is designated SEQ ID NO: 20 and that of the B heavy chain variable region is SEQ ID NO: 21. The nucleotide sequence of the C light chain variable region is designated SEQ ID NO: 23 and that of the C heavy chain variable region is SEQ ID NO: 24.

The corresponding predicted amino acid sequences of these variable chain regions were determined, and are designated SEQ ID NO: 26 (B light chain); SEQ ID NO: 27 (B heavy chain); SEQ ID NO: 29 (C light chain); SEQ ID NO: 30 (C heavy chain). See FIGS. 3 and 4.

Example 9

Determination of Binding Constants for RG1 Antibodies

Kinetic constants ($K_D$, $k_a$ and $k_d$) of mab binding to native RG1 protein were determined by BIAcore using a capture format in which soluble, native RG1 protein was bound to immobilized mab on a sensor chip. ImmunoPure rabbit anti-human IgGFc (Pierce, 31142) was covalently immobilized to the Sensor Chip CM5 (Biacore, BR-1000-12) using standard amine coupling methods. 100 ug/ml antibody diluted in 10 mm acetate, pH 4.0 was used at 5 ul/min. HBS-EP (Biacore, BR-1001-88) was used as mobile phase. Unreacted sites were blocked with ethanolamine. Mabs were diluted to 200 nM with HBS and 50 ul was injected per cycle at 10 ul/min. Serial dilutions of BHK-RG1 (12.5-400 nM) were bound to the immobilized mab. Dissociation kinetics were measured immediately after the antigen injection was completed at 20 ul/min for 8 minutes. The surface was regenerated following each cycle using 25 ul of 10 mm glycine, pH 1.8 and then washed with HBS.

Typically, five concentrations and a media control were run. Data were fit to a 1:1 Langmuir model using the software provided by the instrument manufacturer (BIAevaluation 3.0), and kinetic constants were calculated. Equilibrium constants were in the nanomolar range with favorable dissociation rates ($10^{-4}$ $s^{-1}$). Table 1 shows the kinetic constants for 4 of the human antibodies.

TABLE 1

Kinetic constants of human RG-1 antibodies A, B, C, and D.

| M ab | $K_a$ (1/M s) | $K_d$ (1/s) | $K_D$ (M) |
|---|---|---|---|
| A | $2.3 \times 10^4$ | $1.9 \times 10^{-4}$ | $8.9 \times 10^{-9}$ |
| B | $2.9 \times 10^4$ | $2.3 \times 10^{-4}$ | $8.4 \times 10^{-9}$ |
| C | $2.5 \times 10^4$ | $8.4 \times 10^{-4}$ | $3.36 \times 10^{-8}$ |
| D | $3.17 \times 10^4$ | $2.95 \times 10^{-3}$ | $9.27 \times 10^{-8}$ |

The kinetic constants for these antibodies were determined by fitting a 1:1 Langmuir model to the data obtained from the BIAcore study. $K_a$: association rate (1/s); $k_d$: dissociation rate (1/s) $K_D$: affinity (M)

Example 10

Radiolabeling of RG1 Antibodies

Conjugation of chelator to RG1 antibodies: The bifunctional chelator p-SCN-Benzyl-DTPA (Macrocyclics, Inc.) was covalently attached to antibodies using a method adapted from Nikula et al, *Nucl. Med. Biol., Vol.* 22, No. 3, pp. 387-390, 1995. All reagents and equipment utilized during this procedure were rendered metal-free prior to use in order to avoid inactivation of the chelator. All solutions were prepared with low metal reagents, high purity (MilliQ) water and Chelex treated to remove trace metals. All equipment was rinsed with 10 mM EDTA and then extensively rinsed with MilliQ water.

Purified mabs (~20 mg) were first treated with 1 mM EDTA for 1 hour at room temperature to remove any metals prior to buffer exchange into 50 mM Carbonate buffer, 150 mM NaCl, pH 8.5 using a Pharmacia 26/10 desalting column on an AKTA chromatography system. Antibody containing fractions were pooled and concentrated to approximately 2 mg/ml by ultrafiltration (Centricon 30). A 100 mg/ml p-SCN-Benzyl-DTPA stock solution was freshly prepared in anhydrous DMSO. A 50-100 fold molar excess of DTPA was used in the conjugation reaction, which was allowed to proceed overnight at room temperature. The reaction mixture was then buffer exchanged into 50 mM Na Acetate, 150 mM NaCl, pH 6.5 (Radiolabeling Buffer) and concentrated to at least 3 mg/ml by ultrafiltration. Antibody conjugates were stable in this buffer for weeks at 4 degrees C. Protein concentration was determined by BCA and antigen binding activity was verified by ELISA.

Radiolabeling of RG1 antibodies: DTPA-conjugated antibodies were radiolabeled with $^{90}$Y or $^{111}$In, under metal-free conditions, for use in in vivo studies in tumor-bearing animals. Typically, 10 mg of antibody conjugate was mixed with 10 mCi of [$^{90}$Y]Cl$_3$ or [$^{111}$In]Cl$_3$ (PerkinElmer Life Sciences) for 1 hour at room temperature with gentle mixing behind heavy shielding. EDTA was added to 1 mM and incubated for 10 minutes at room temperature. The reaction mixture was run over a Pharmacia 26/10 Desalting column, that had been preequilibrated in metal-free PBS, in order to separate the radiolabeled antibody from unbound $^{90}$Y and to exchange buffer. One ml fractions were collected and antibody containing fractions were pooled. Protein concentration was determined by BCA. Total radioactivity in a 1 ul sample was determined using a liquid scintillation counter for $^{90}$Y or a gamma counter for $^{111}$In. Specific activity was calculated as mCi per mg of protein, and typically ranged from 0.25 to 1.0 mCi/mg. Radiological purity was determined by instant thin layer chromatograph (ITLC) according to Nikula et al, *Nucl. Med. Biol.* 22: 387-390, 1995. Typically, greater than 98% of the radioactivity was associated with the protein. Antigen binding activity of the radioconjugate was determined by ELISA against an unconjugated antibody standard ($^{90}$Y conjugates), or using a solid phase radioimmune binding assay on immobilized RG1 protein ($^{111}$In conjugates). In all cases, antigen binding of the radioconjugates was indistinguishable from that of the unconjugated antibody.

Example 11

Tumor Specific Accumulation of $^{111}$In-Labeled RG1 Antibodies

Tumor xenografts were established by s.c. injection of 1×0-7 LNCaP cells in matrigel into the flank of 5-6 week-old male athymic nude mice. Biodistribution studies were performed when the tumors reached a volume of 150-400 mm$^3$ (approximately 4-6 weeks after tumor cell inoculation). $^{111}$In-labeled I human RG1 antibodies (C, B, A) and a non-specific human IgG$_1$ control antibody (specific activities, 0.3 mCi/mg) were administered intravenously into four groups of 12 mice bearing LNCaP xenografts. Mice were exsanguinated by cardiac puncture prior to dissection. Blood, tumor and all major organs were removed, weighed on an analytical balance, and the radioactivity was counted in a gamma-counter. The whole body clearance was determined by summing the radioactivity measured in blood, individual organs, and in the remaining carcass. All data were corrected for radioisotope decay. Results were expressed as percentage injected dose per gram of tissue. RG1 specific antibodies show a high tumor specific accumulation (See FIG. 1).

Example 12

Tumor Growth Inhibition with $^{90}$Y-Labeled RG1 Antibodies

Figure 2:
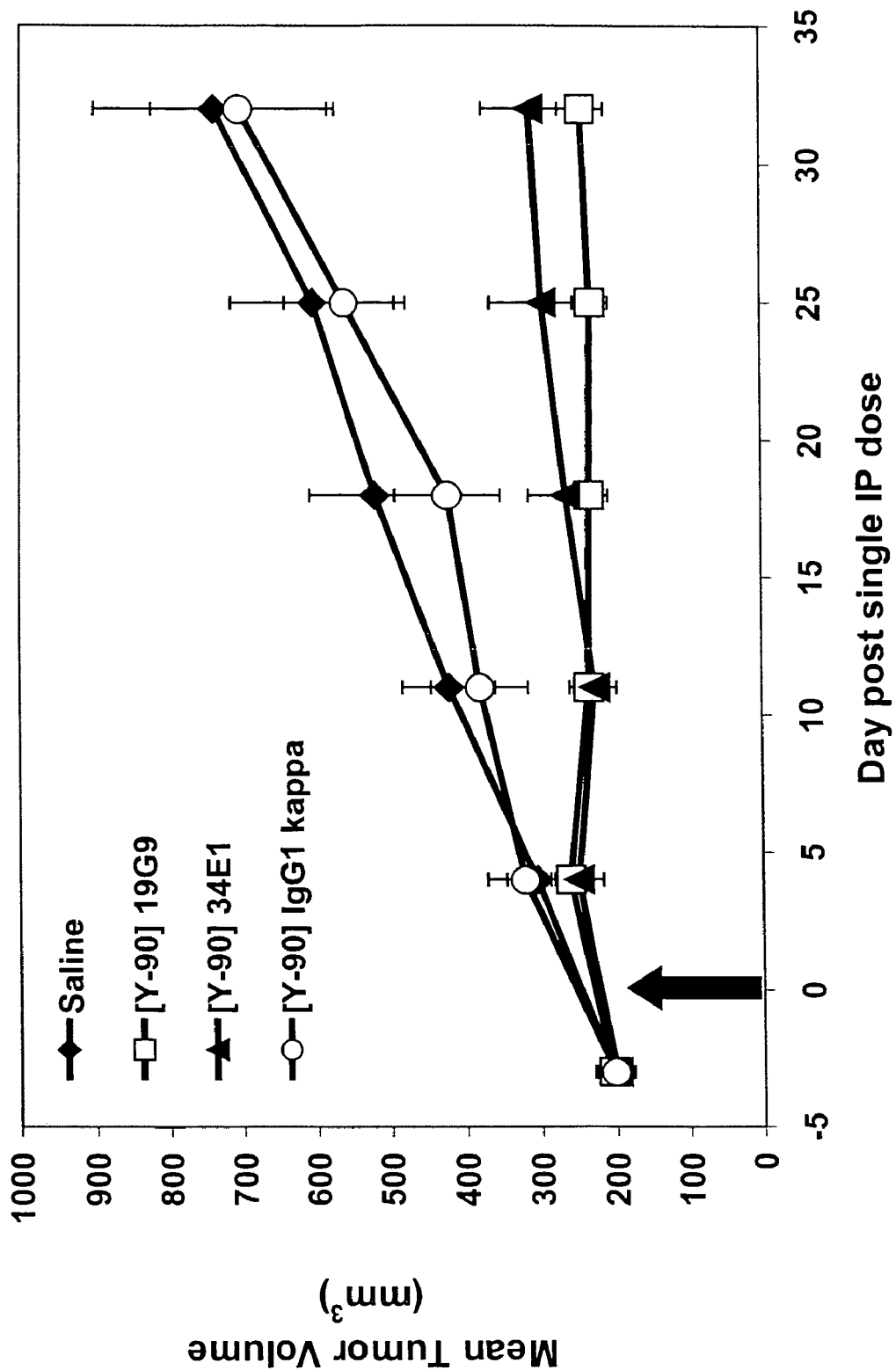
FIG. 2: Anti-tumor effect of $^{90}$Y labeled RG1 Antibodies: LNCaP tumor bearing animals were injected with $^{90}$Y labeled antibodies (anti-RG1 antibodies B and C or non-specific IgG$_1$, specific activity, 0.5 mCi/mg). A single dose of 125 µCi $^{90}$Y-labeled RG1 antibody (B,C) was administered i.p. Mice were sacrificed at day 32 and tumors excised and weighed. (See Example 12)

Tumor xenografts were established by s.c. co-inoculation of 1×10$^{-7}$ LNCaP cells in matrigel into the flank of 5-6 week-old male athymic mice. Treatment was initiated when the tumors reached a volume of 50-350 mm$^3$ (5 weeks after tumor cell inoculation). Tumor bearing animals were evenly distributed into four treatment groups (n=13/group). A single i.p. injection of radiolabeled antibody B, C, and non-specific IgG$_1$ (125 μCi/animal) was administered into mice bearing LNCaP xenografts. The fourth treatment group was given a saline i.p. injection. The effect of $^{90}$Y labeled RG1 specific antibodies on the growth of the LNCaP-derived tumors was monitored for 32 days after injection. At that time, animals were sacrificed and tumors were taken out and weighed. Health status was determined by monitoring body weight. A single administration of $^{90}$Y labeled specific human RG1 antibodies produced a significant inhibition of tumor growth when compared to the results seen in the animals injected with $^{90}$Y labeled nonspecific antibody or the vehicle control. (See FIG. 2).

Example 13

Cloning and Expression of RG1 Antibodies in Cho Cells

Mutagenesis: Site-directed mutagenesis of the wild-type cDNA encoding variable regions of anti-RG1 antibody B and C was carried out to generate allotypes that are more frequently expressed in humans. Multisite-directed mutagenesis was performed using a kit sold by Stratagene (QUICK-CHANGE®) to conduct the mutagenesis, with TOPO/BVH and TOPO/CVH (Medarex) as templates. Primers (GGG-GAGGCTTGGTA<u>CAA</u>CCTGGGGGGTCCCTGAG; SEQ ID NO: 14) and (GAACAGCCTGAGAGCCGAGGAC<u>ACG</u>GCT<u>GTG</u>TATTACTGTGCAAG; SEQ ID NO: 15) were used to introduce the point mutations H13Q, M90T and MB3V into B cDNA (BVH_3m); and H13Q, M90T into C cDNA (CVH_2m). Mutations were confirmed by DNA sequence analysis and resulted in the mutant heavy chain variable regions with sequences of SEQ ID NO: 22 and SEQ ID NO: 25, respectively. The predicted amino acid sequences for these two heavy chain variable regions are given by SEQ ID NOS: 28 and 31, respectively.

Construction of expression vectors: The expression vector of pIE_SRγ1fa (Medarex) contains cDNAs encoding CH and CL regions of human IgG1 (fa haplotype) and kappa chains, respectively. To allow for in frame cloning of B and C light chain variable regions into pIE_SRγ¹fa was, the primer pair BVK_F (GGG<u>AAGCTT</u>GCCACCATGGAAACCCCAG CG; SEQ ID NO: 16) and BVK_R (CAGT<u>CGTACG</u>TTT GATCTCCACCTTGGTCC; SEQ ID NO: 17) was used to introduce compatible HindIII/Bsiw sites (under line) at the 5' and 3' ends, respectively, of BVL and CVL cDNA. The resulting PCR-generated $V_L$ cDNAs were cloned into the HindIII/Bsiw site of pIE-SRγ1fa to create pIE/BVL and CVL. The same strategy was used for constructing in frame $V_H$ fusions (including BVH, BVH_3m, CVH and CVH_2 m) into pIE/BVL and CVL. Briefly, the primer pair of CVH_F (GTCAG-GAT<u>GCGGCCGC</u>CACCATGGAGTTGTGCTGAGCT; SEQ ID NO: 18) and CVH_R (ACCGAT<u>GGGCCC</u>TTGGTGGA; SEQ ID NO: 19) was used to introduce NotI/ApaI sites at the ends of PCR-amplified VH cDNA. The PCR products were digested with NotI/ApaI and inserted upstream of the CH region of pIE/BVL and pIE/CVL ensuring that the VH regions were in frame with CH region in the respective pIE derivatives. The final constructs were named pIE/B, pIE/B_3m, pIE/C and pIE/C_2m. All inserts have been verified by DNA sequence analysis.

Transfection and selection/amplification of DG44 and DXB11 cells. About 4×10$^6$ DG44 and DXB11 cells supplemented with F12 medium and 5% FCS were plated on P100 dishes one day before transfection. Transfections were carried out using Lipfectamine 2000 (Invitrogen) and 24 μg linearized plasmid DNA (pIE/B_3m or pIE/C_2m)/P100. The medium was changed 4 hours after transfection. Selective conditions were applied approximately 24 h post-transfection.

Selection was first carried out with MEM medium containing 5% dialyzed FBS, 2 mM L-glutamine and G418 (400 ug/ml), but lacking ribonucleosides and deoxyribonucleosides. Reaching a confluency of about 90% cells were split into 4×P100 dishes and co-selected with G418 plus methotrexate at various concentrations. After one week, the surviving cells were plated into 96-well plates at 100-cells/plate in the presence of co-selection medium. Surviving clones were screened by ELISA for expression of recombinant antibody. Gene copy number of 10 clones exhibiting the highest expression levels was amplified by consecutive selection in the presence of increasing concentrations of methotrexate and chosen clones adapted to serum free medium for preparation of a master cell bank.

All publications and patents mentioned in the above specification are herein incorporated by reference. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for treating a disease-state in a human patient, wherein the disease-state is associated with expression of an RG1 polypeptide having the amino acid sequence of SEQ ID NO: 2, which method comprises administering to the patient a therapeutically effective amount of an antibody or a fragment thereof, wherein
(i) the isolated antibody or a fragment thereof comprises
a) a light chain variable region comprising the amino acid sequence of SEQ ID NO: 26 or SEQ ID NO: 29, or
b) a heavy chain variable region comprising the amino acid sequence of SEQ ID NO: 27, SEQ ID NO: 28, SEQ ID NO: 30, or SEQ ID NO: 31 or
c) a light chain variable region having the amino acid sequence of SEQ ID NO: 26 and a heavy chain variable region having the amino acid sequence of SEQ ID NO: 27 or SEQ ID NO: 28, or
d) a light chain variable region having the amino acid sequence of SEQ ID NO: 29 and a heavy chain variable region having the amino acid sequence of SEQ ID NO: 30 or SEQ ID NO: 31,
thereby treating the disease-state in the human patient.

2. A method for treating a disease-state in a human patient, wherein the disease-state is associated with expression of an RQ1 polypeptide having the amino acid sequence of SEQ ID NO: 2, which method comprises administering to the patient a therapeutically effective amount of an antibody or a fragment thereof, wherein
(i) the isolated antibody or a fragment thereof comprises:
a) a light chain CDR3 sequence comprising the amino acid residues 110 to 117 of SEQ ID NO: 26,
b) a heavy chain CDR3 sequence comprising the amino acid residues 117 to 132 of SEQ ID NO: 27,
c) a light chain CDR1 sequence and CDR2 sequence, wherein the sequences comprise the amino acid residues 44 to 55 of SEQ ID NO: 26 and 71 to 77 of SEQ ID NO: 26, respectively, and
d) a heavy chain CDR1 sequence and CDR2 sequence, wherein the sequences comprise the amino acid residues 50 to 54 of SEQ ID NO: 27 and 69 to 84 of SEQ ID NO: 27, respectively,
thereby treating the disease-state in the human patient.

3. A method for treating a disease-state in a human patient, wherein the disease-state is associated with expression of an RG1 polypeptide having the amino acid sequence of SEQ ID NO: 2, which method comprises administering to the patient a therapeutically effective amount of an antibody or a fragment thereof, wherein (i) the isolated antibody or a fragment thereof comprises:
a) a light chain CDR3 sequence comprising the amino acid residues 110 to 117 of SEQ ID NO: 29,
b) a heavy chain CDR3 sequence comprising the amino acid residues 117 to 126 of SEQ ID NO: 30,
c) a light chain CDR1 sequence and CDR2 sequence, wherein the sequences comprise the amino acid residues 44 to 55 of SEQ ID NO: 29 and 71 to 77 of SEQ ID NO: 29, respectively, and
d) a heavy chain CDR1 sequence and CDR2 sequence, wherein the sequences comprise the amino acid residues 50 to 54 of SEQ ID NO: 30 and 69 to 84 of SEQ ID NO: 30, respectively,
thereby treating the disease-state in the human patient.

4. The method of claims 1, 2 or 3, wherein the disease-state is cancer.

5. The method of claims 1, 2 or 3, wherein the cancer is prostate cancer, renal cancer, ovarian cancer or colorectal cancer.

6. The method of claims 1, 2 or 3, wherein the antibody fragment is selected from the group consisting of Fv, F(ab'), F(ab')$_2$, scFv, single chain antibodies and P(ab')$_2$ fragments.

7. The method of claims 1, 2 or 3, wherein the antibody or a fragment thereof is conjugated to a therapeutic agent.

8. The method of claim 7, wherein the therapeutic agent is a cytotoxic agent.

9. The method of claim 8, wherein the cytotoxic agent is selected from the group consisting of ricin, doxorubicin, daunorubicin, ethidium bromide, mitomycin, etoposide, tenoposide, vincristine, vinblastine, colchicine, dihydroxy anthracin dione, actinomycin D, diphtheria toxin, *Pseudomonas* exotoxin (PE) A, PE40, ricin, akin, glucocorticoid and radioisotopes.

10. The method of claim 8, wherein the cytotoxic agent is $^{90}$Y or $^{177}$Lu.

11. The method of claim 7, wherein the conjugation of the antibody with the therapeutic agent utilizes a chelator selected from the group consisting of p-SCN-Benzyl-DTPA and derivatives thereof, 1,4,7,10-tetraazacyclododecane-N,N',N'',N'''-tetra-cetic acid (DOTA) and derivatives thereof, and 1,4,7-triazacyclononane-N,N',N''-triacetic acid (NOTA) and derivatives thereof.

12. The method of claim 11, wherein the chelator used is cyclohexyl-DTPA (CHX-A''-DTPA) or MX-DTPA (1B4M-DTPA).

* * * * *